United States Patent
Nagase et al.

(10) Patent No.: US 8,372,587 B2
(45) Date of Patent: Feb. 12, 2013

(54) PROLIFERATIVE DISEASE DETECTION METHOD

(75) Inventors: Hiroki Nagase, Tokyo (JP); Yui Shinojima, Tokyo (JP); Tadashi Terui, Tokyo (JP)

(73) Assignee: Nihon University, Tokyo (JP)

( * ) Notice: Subject to any disclaimer, the term of this patent is extended or adjusted under 35 U.S.C. 154(b) by 186 days.

(21) Appl. No.: 12/937,407

(22) PCT Filed: Apr. 14, 2009

(86) PCT No.: PCT/JP2009/057524
§ 371 (c)(1),
(2), (4) Date: Oct. 12, 2010

(87) PCT Pub. No.: WO2009/128453
PCT Pub. Date: Oct. 22, 2009

(65) Prior Publication Data
US 2011/0033864 A1 Feb. 10, 2011

(30) Foreign Application Priority Data
Apr. 14, 2008 (JP) ................. 2008-104321

(51) Int. Cl.
*C12Q 1/68* (2006.01)
*C07H 21/02* (2006.01)
*C07H 21/04* (2006.01)

(52) U.S. Cl. ...... 435/6.11; 435/6.4; 435/6.14; 536/23.5; 536/24.1; 536/24.31

(58) Field of Classification Search ........................ None
See application file for complete search history.

(56) References Cited

U.S. PATENT DOCUMENTS
2009/0215709 A1 * 8/2009 Van Criekinge et al. ....... 514/34

FOREIGN PATENT DOCUMENTS
| WO | WO 96/35704 A1 | 11/1996 |
| WO | WO 97/46705 A1 | 12/1997 |
| WO | WO 98/56952 A1 | 12/1998 |
| WO | WO 03/080863 A1 | 10/2003 |

OTHER PUBLICATIONS

Rechache et al. The Journal of Clinical Endocrinology & Metabolism. Published online Apr. 3, 2012. vol. 97, available via url: <jcem.endojournals.org/content/early/2012/04/03/jc.2011-3298.full.pdf>.*
Kim et al. The Korean J Pathol. 2010. 44: 315-321.*
Ushijima et al. Nature Reviews. 2005. 5: 223-231.*
Yang et al. J. Cancer Res Clin Oncol. 2009. 135: 919-924.*
Nishiyama et al. Cancer Biology and Therapy. 2005. 4: 440-448.*
Smiraglia et al. Human Molecular Genetics. 2001. 10: 1413-1419.*
Battagli et al. Cancer Research. Dec. 2003. 63: 8695-8699.*
Erlich et al Oncogene 2002. 21: 5400-5413; p. 5401.*
Muller-Tidow et al. FEBS Letters. 2001. 490: 75-78.*
Byun et al., "Examination of IGF2 and H19 Loss of Imprinting in Bladder Cancer," Cancer Res. (Nov. 15, 2007) vol. 67, No. 22, pp. 10753-10758.
Dejeux et al., "Rapid Identification of Promoter Hypermethylation in Hepatocellular Carcinoma by Pyrosequencing of Etiologically Homogenous Sample Pools," Journal of Molecular Diagnostics (Sep. 2007) vol. 9, No. 4, pp. 510-520.
European Search Report issued Sep. 13, 2011, in European Patent Application No. 09731493.4.
International Search Report for PCT/JP2009/057524 mailed May 19, 2009.
Kawakami et al., "Erasure of methylation imprint at the promoter and CTCF-binding site upstream of H19 in human testicular germ cell tumors of adolescents indicate their fetal germ cell origin", Oncogene, 2006, vol. 25, No. 23, pp. 3225-3236.
Song et al., "Association of tissue-specific differentially methylated regions (TDMs) with differential gene expression", Proc. Natl. Acad. Sci., USA, Mar. 1, 2005, vol. 102, No. 9, pp. 3336-3341.
Wu et al., "Zygote arrest 1 (Zar1) is a novel maternal-effect gene critical for the oocyte-to-embryo transition", Nature Genetics, Feb. 2003, vol. 33, No. 2, pp. 187-191.
Wu et al., "Zygote Arrest 1 (Zar1) is an Evolutionarily Conserved Gene Expressed in Vertebrate Ovaries", Biology of Reproduction 69, 2003, pp. 861-867.

* cited by examiner

*Primary Examiner* — Carla Myers
(74) *Attorney, Agent, or Firm* — Birch, Stewart, Kolasch & Birch, LLP

(57) ABSTRACT

In the present invention, the methylation of the genomic DNA a Zar1 gene specifically found in proliferative disease is used as a marker. Specifically, the present invention provides a method for detecting proliferative disease, which comprises detecting the methylation of the genomic DNA of a Zar1 gene in a biological sample. There is thereby provided a method for detecting proliferative disease, using a marker having a high detection rate and a low false positive rate.

6 Claims, 15 Drawing Sheets

FIG. 1

PROLIFERATIVE DISEASE DETECTION METHOD

TECHNICAL FIELD

The present invention relates to a method for detecting proliferative disease such as cancer.

BACKGROUND ART

Methods for detecting cancer include a method of detecting a cancer-specific antigenic substance in blood, a method of identifying a cancer specific genetic change by a DNA amplification method or the like, and other methods. These are methods, in which cancer is detected using a cancer-specific antigenic substance existing in blood or a cancer-specific genetic change as a tumor marker.

As such cancer-specific antigenic substances existing in blood, there are many types of antigenic substances such as a glycoprotein, a hormone and an enzyme. Among these substances, those which have been actively applied in clinical sites include a prostate specific antigen (PSA), a carcinoembryonic antigen (CEA), CA19-9, CA50, Span-1, Dupan-2 and the like.

Moreover, as such cancer-specific genetic changes, cancer-specific sequences found in a RAS oncogene or a BRCA1 cancer suppressor gene haven been known, for example. An attempt to use these cancer-specific sequences as tumor markers has gradually progressed.

However, conventional tumor markers have room for improvement in terms of cancer detection rates and false positive rates. For example, CEA and CA19-9, which are used as tumor markers for colon cancer, also exhibit high values due to the inflammation of a digestive system, such as hepatitis and pancreatitis. Thus, there is a fear that these tumor markers detect the inflammation of a digestive system incorrectly as colon cancer. Furthermore, there exist tumors (negative tumors) that cannot be detected by CEA or CA19-9, although they are colon cancers.

Patent Document 1 describes a method for detecting cellular proliferative disease, which comprises allowing a reagent for detecting the methylation of polynucleotide p16 to come into contact with cells in tissues.

Patent document 2 describes a method for detecting the methylation of DNA, using Methylation Specific PCR (MSP).

Patent Document 3 describes a method for detecting the methylation of a cytosine residue, using Methylation-Sensitive Single Nucleic Primer Extension (Ms-SNuPE).

Patent Document 4 describes a method for detecting the methylation of genomic DNA. In this method, target DNA in the genomic DNA is amplified, while maintaining the methylated state thereof, and the amplified DNA is then analyzed using a mass spectrometer, so as to detect the methylation of the target DNA.

Non-Patent Document 1 describes that a ZAR1 gene in the ovum of mother is an important gene essential for the early stage at which a fertilized ovum is matured to become an embryo.

Non-Patent Document 2 describes that such ZAR1 gene is well preserved as an expression gene specific to the ovary of a vertebrate animal.

PRIOR ART DOCUMENTS

Patent Documents

Patent Document 1: WO1996/035704
Patent Document 2: WO1997/046705
Patent Document 3: WO1998/056952
Patent Document 4: WO2003/080863

Non-Patent Documents

Non-Patent Document 1: Zygote arrest 1 (Zar1) is a novel maternal-effect gene critical for the oocyte-to-embryo transition. Wu X, Viveiros M M, Eppig J J, Bai Y, Fitzpatrick S L, Matzuk M M. Nat Genet. 33(2):187-91 (2003).
Non-Patent Document 2: Zygote Arrest 1 (Zar1) is an evolutionarily conserved gene expressed in vertebrate ovaries. Xuemei Wu, Pei Wang, Christopher A. Brown, Carolyn A. Zilinski, and Martin M. Matzuk BIOLOGY OF REPRODUCTION 69, 861-867 (2003)

SUMMARY OF THE INVENTION

Problem to be Solved by the Invention

Under the aforementioned circumstances, it has been desired to develop a method for detecting proliferative disease, using a marker having a high detection rate and a low false positive rate.

Means for Solving the Problem

As a result of intensive studies directed towards overcoming the aforementioned problem, it has been found that proliferative disease-specific methylation is found at a high frequency in the genomic DNA of a Zar1 gene, and that proliferative disease can be detected at high detection rates and at low false positive rates, using the methylation as a marker. The present invention has been completed based on these findings.

Specifically, the present invention provides a method for detecting or diagnosing proliferative disease as described below:

(1) A method for detecting or diagnosing proliferative disease, which comprises detecting the methylation of the genomic DNA of a Zar1 gene in a biological sample.
(2) The method according to (1) above, wherein the genomic DNA is a genomic DNA in the peripheral region of the promoter of the Zar1 gene.
(3) The method according to (2) above, wherein the genomic DNA is at least one CpG sequence existing in the peripheral region of the promoter of the Zar1 gene.
(4) The method according to any one of (1) to (3) above, wherein the biological sample is a biological sample derived from a mammal.
(5) The method according to (4) above, wherein the mammal is a human.
(6) The method according to (5) above, which comprises detecting the methylation of at least one CpG sequence selected from among the $60^{th}$ to $187^{th}$ CpG sequences counted from the 5'-side (5'-terminal side) in the peripheral region of the promoter of the Zar1 gene in the human-derived biological sample.
(7) The method according to (6) above, which comprises detecting the methylation of at least one CpG sequence selected from among the $118^{th}$ to $166^{th}$ CpG sequences counted from the 5'-side in the peripheral region of the promoter of the Zar1 gene in the human-derived biological sample.
(8) The method according to any one of (1) to (7) above, wherein the proliferative disease is cancer.
(9) The method according to (8) above, wherein the cancer is at least one selected from the group consisting of malignant melanoma, esophageal cancer, neuroblastoma, glioblastoma, glioma, Wilms tumor, cutaneous squamous cell carcinoma, lung adenocarcinoma, lung squamous cell carcinoma, breast cancer, osteosarcoma, rhabdosarcoma, pancreatic cancer, colon cancer, renal cell carcinoma, prostatic cancer, urothelial carcinoma, bladder cancer, cervical cancer, squamous cell carcinoma of the tongue, and hepatoblastoma.

(10) The method according to (9) above, wherein the cancer is malignant melanoma, neuroblastoma, hepatoblastoma, or bladder cancer.

(11) The method according to any one of (1) to (10) above, in which the above-detected methylation frequency of the ZAR1 gene in the biological sample is compared with the methylation frequency of the genomic DNA of a ZAR1 gene in a normal cell, and when the methylation frequency of the ZAR1 gene is higher than the methylation frequency of the genomic DNA of the ZAR1 gene in the normal cell, it is determined that the biological sample has become cancerous.

(12) The method according to any one of (11) above, in which when the methylation frequency of the ZAR1 gene is higher than the methylation frequency of the genomic DNA of the ZAR1 gene in the normal cell, and further, the methylation frequency is 50% or more, it is determined that the biological sample has become cancerous.

Effects of the Invention

According to the present invention, a method for detecting proliferative disease using a novel marker is provided. The marker used in the method for detecting proliferative disease of the present invention is advantageous in that it has a high detection rate and a low false positive rate, etc.

BRIEF DESCRIPTION OF THE DRAWINGS

FIG. 1 is a view showing the results obtained by analyzing 30 types of human-derived samples, in terms of the presence or absence of methylation in the 27 gene regions thereof.

In FIG. 2, "100%" indicates that all cytosines in CpG sequences are methylated, and "0%" indicates that all cytosines in CpG sequences are demethylated.

BEST MODE FOR CARRYING OUT THE INVENTION

Figure 2:
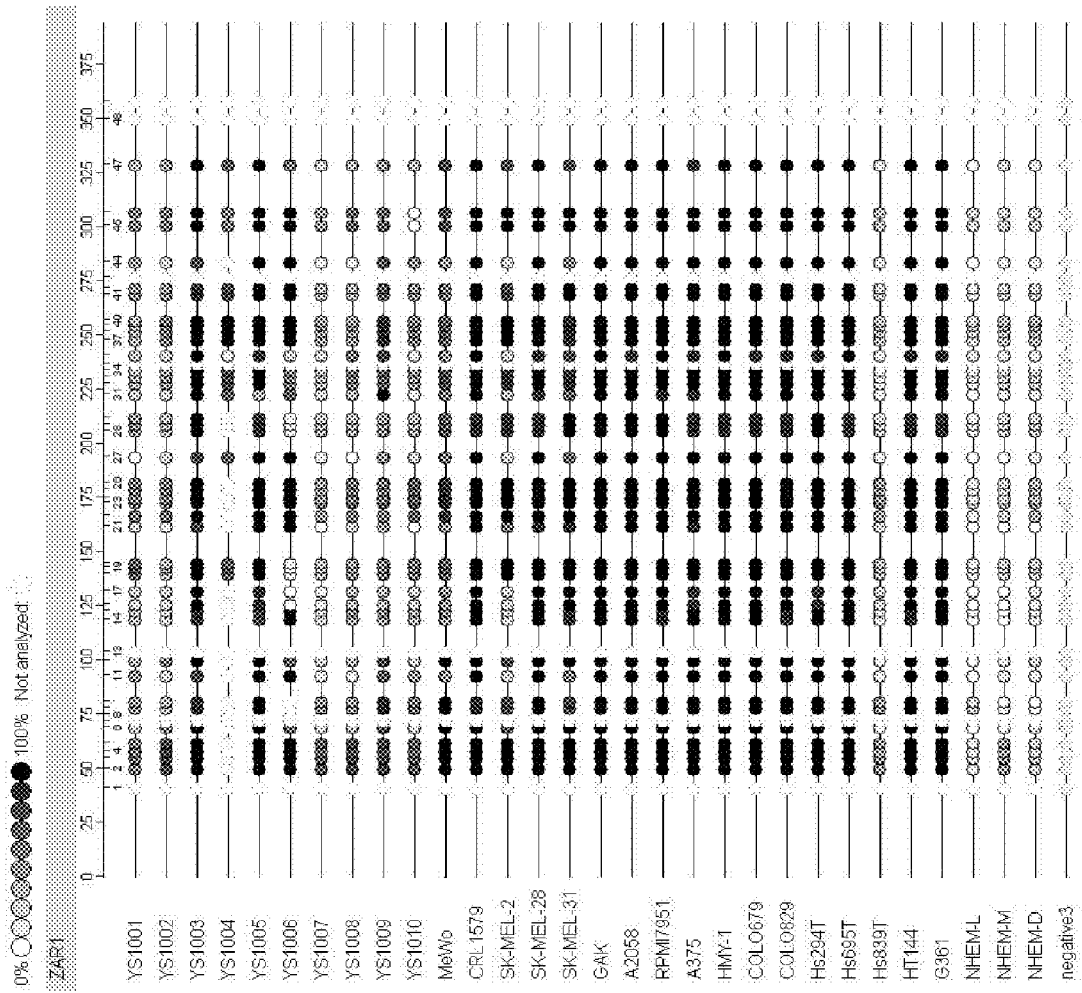
FIG. 2 is a view showing the results obtained by analyzing Skin 15 of FIG. 1, in terms of the presence or absence of methylation.

The present invention will be described in detail below.

It is to be noted that all publications cited in the present specification, which include prior art documents and patent documents such as laid-open application publications and patent publications, are incorporated herein by reference in their entirety. The present specification includes the contents as disclosed in the specification of Japanese Patent Application No. 2008-104321, which is a priority document of the present application.

1. SUMMARY OF THE PRESENT INVENTION

The method for detecting or diagnosing proliferative disease of the present invention is a method comprising detecting the methylation of the genomic DNA of a Zar1 gene in a biological sample. The genomic DNA whose methylation is to be detected is, for example, a genomic DNA in the peripheral region of the promoter of the Zar1 gene, and it is preferably at least one CpG sequence existing in the peripheral region of the promoter of the Zar1 gene. In addition, the aforementioned peripheral region of the promoter is, for example, a region comprising at least two CpG sequences. It is preferably a region in which a CpG island is present, and more preferably a region in which a CpG island comprising 187 CpG sequences in a human Zar1 gene is present. Further preferably, the genomic DNA whose methylation is to be detected is at least one CpG sequence selected from among the $60^{th}$ to $187^{th}$ CpG sequences, and particularly, the $118^{th}$ to $166^{th}$ CpG sequences, counted from the 5'-side, existing in the peripheral region of the promoter of the aforementioned human Zar1 gene. That is to say, in several embodiments of the present invention, the methylation of cytosine of the genomic DNA of a Zar1 gene in a biological sample is used as a marker for detecting proliferative disease.

The aforementioned marker for detecting proliferative disease of the present invention has been identified as follows. Malignant melanoma has been known as a refractory tumor that is likely to become metastatic and is intractable to treatment. Among cancers such as skin cancer, malignant melanoma has a high mortality rate, and thus it has been desired to rapidly establish preventive, diagnostic and therapeutic methods and to clarify the cause of the disease.

Under such circumstances, the present inventors have conducted intensive studies directed towards establishing a method for diagnosing or detecting proliferative disease such as malignant melanoma. The inventors have focused on the epigenetic change of a gene, which had gathered attention in recent years as a candidate for a novel proliferative disease-detecting marker, and particularly, on the abnormal methylation of the peripheral region of the promoter of the gene. With regard to such abnormal methylation of the peripheral region of the gene promoter, a mechanism whereby the peripheral region of the promoter of a cancer suppressor gene is methylated and the cancer suppressor gene thereby becomes inactivated, a mechanism whereby the peripheral region of the promoter of an oncogene is demethylated and the oncogene thereby becomes inactivated, and the like, have come to be known. Thus, the methylation of the peripheral region of the gene promoter has become a focus of attention as a novel marker candidate. For example, in the case of malignant melanoma as well, the abnormal methylation of the peripheral region of the gene promoter is considered to play an important role for the development of the disease.

Using model mice, a study group including the present inventors has discovered a large number of genomic regions, in which DNA methylation has altered, in a testis-, ovary- and placenta-specific manner, and also in a cancer-specific manner. The study group has then identified a gene locus, which is likely to specifically express in the testis, cancer, and the like, as a result of the methylation or demethylation of the peripheral region of the gene promoter.

Moreover, using specimens collected from malignant melanoma patients and various types of cell lines, the present inventors have searched for DNA methylation in human genomic regions homologous to the above-mentioned regions. Consequently, the inventors have identified a Zar1 gene, which is likely to express specifically for proliferative disease such as cancer, as a result of the methylation or demethylation of the peripheral region of the gene promoter.

Methylation was cancer-specifically observed in the genomic DNA of the Zar1 gene. In particular, in the peripheral region of the promoter of the Zar1 gene, such methylation was observed cancer-specifically at a high frequency. Thus, using, as a marker, the methylation of the genomic DNA of the Zar1 gene in a biological sample, preferably the methylation of the genomic DNA in the peripheral region of the promoter of the Zar1 gene, more preferably the methylation of cytosine in at least one CpG sequence existing in the peripheral region of the promoter of the Zar1 gene, proliferative disease can be detected or diagnosed at high detection rates and at low false positive rates.

Furthermore, an increase in the expression of Zar1 was found in several malignant melanoma cell lines. On the other hand, such increase in the expression of Zar1 was not found in normal human melanocyte cell lines. From these results, it is anticipated that the Zar1 gene is associated with cancerogenesis.

2. PERIPHERAL REGION OF PROMOTER OF ZAR1 GENE

A gametogenesis factor, Zygote Arrest 1 (ZAR1), has been known to specifically express in egg cells in the ovary of a mammal such as a human and to be associated with the changes of the egg cells to fetal cells. Such Zar1 gene encodes the aforementioned ZAR1. Among the Zar1 genes of mammals, the sequence of a DNA encoding human ZAR1 is as shown in SEQ ID NO: 1 (GenBank Accession No. NC_000004). In addition, the amino acid sequence of human ZAR1 is as shown in SEQ ID NO: 2.

In the present invention, the methylation of the genomic DNA of a Zar1 gene, preferably, the methylation of the genomic DNA in the peripheral region of the promoter of such Zar1 gene, and more preferably, the methylation of at least one CpG sequence existing in the peripheral region of the promoter of such Zar1 gene, is used as a marker. Herein, the "peripheral region of the promoter of a Zar1 gene" means a region containing at least a portion of the promoter region of a Zar1 gene, and preferably, a CpG island is present in such region. In the case of humans, the peripheral region of the promoter of the Zar1 gene corresponds to, for example, a region ranging from 191 bp upstream to 1281 bp downstream of the transcription initiation point of the Zar1 gene, in which a CpG island is present (FIG. 8).

Moreover, in the case of mammals other than humans, for example, in the case of mice, the peripheral region of the promoter of the Zar1 gene corresponds to a region ranging from 56 bp upstream to 794 bp downstream of the transcription initiation point of the Zar1 gene, in which a CpG island is present (UCSC genome bioinformatics http://genome.ucsc.edu Kent W J, Sugnet C W, Furey T S, Roskin K M, Pingle T H, Zahler A M and Haussler D., The human genome browser at UCSC. Genome Research 12(6), 996-1006 2002).

The "CpG island" means a region on the genome, in which CpG sequences are present at a high frequency. More specifically, the CpG island is defined as a region consisting of 200 or more nucleotides, which has a CpG content of 50% or more. In general, a CpG sequence undergoes the methylation of cytosine. In a CpG island, however, a CpG sequence does not generally undergo such methylation of cytosine.

Figure 6:
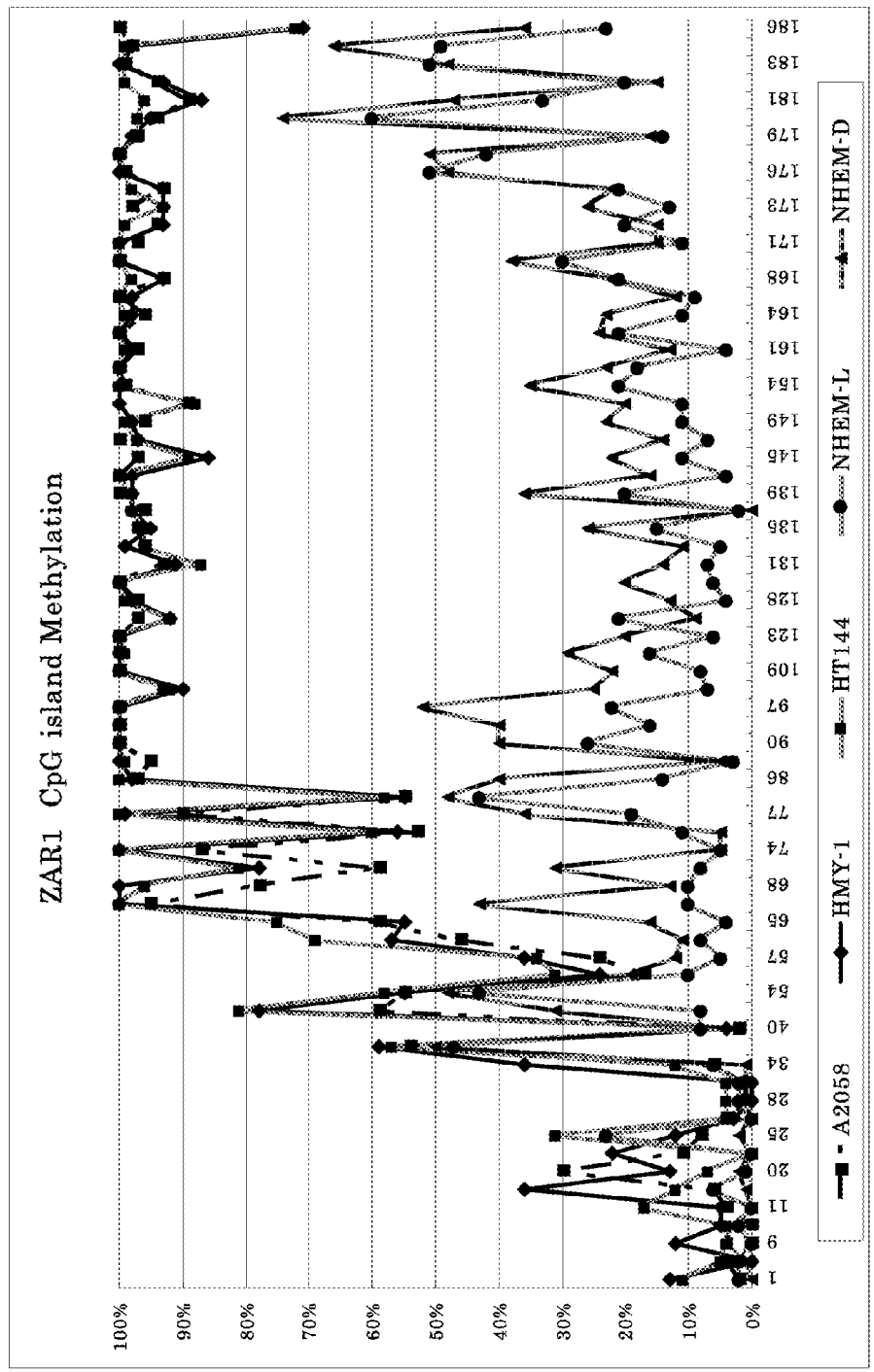
FIG. 6 is a graph showing the methylation frequency (mean value) of the $1^{st}$ to $187^{th}$ CpG sequences counted from the 5'-side in the peripheral region of the promoter of the Zar1 gene in each of 4 types of human-derived samples.
Figure 7:
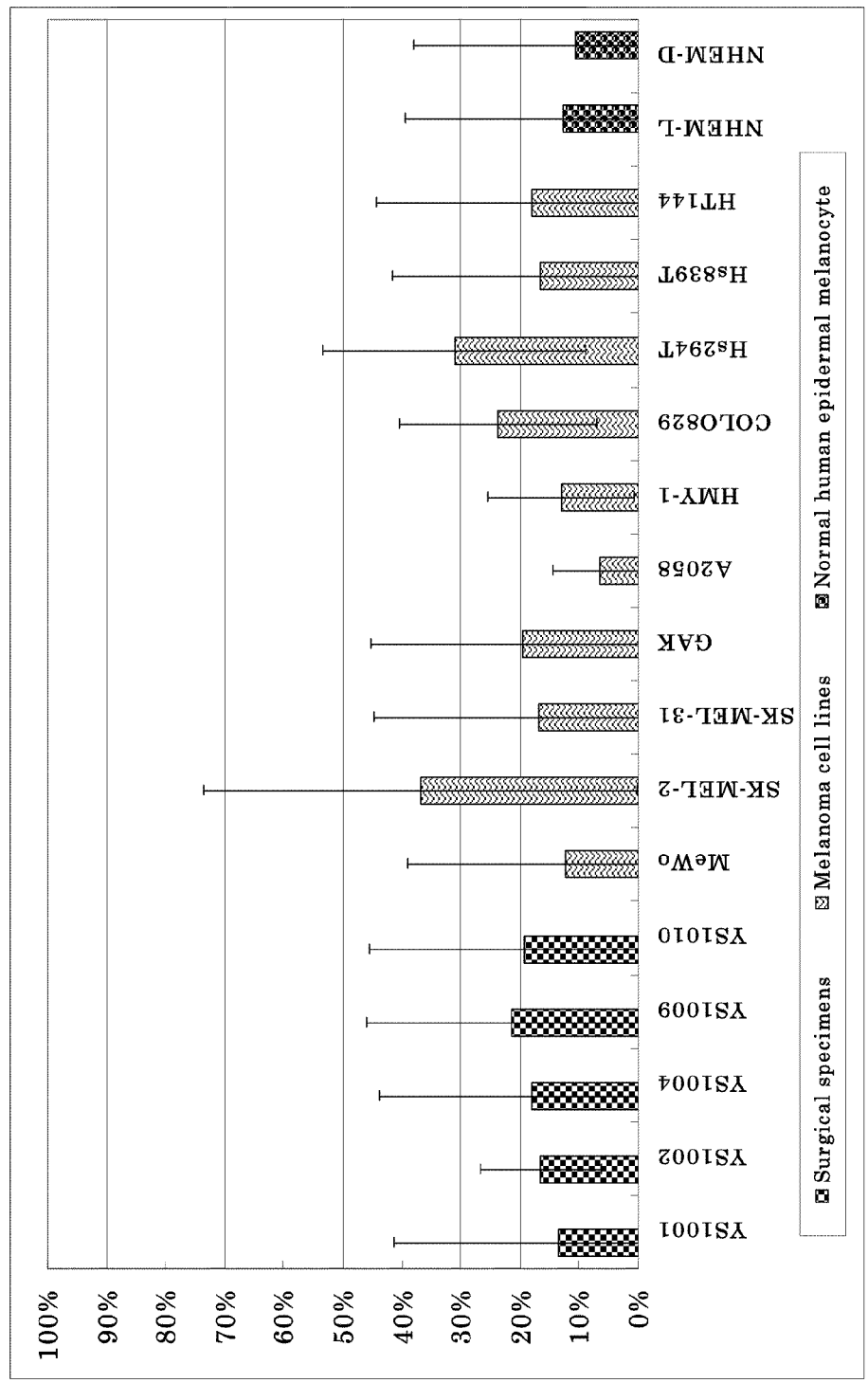
FIG. 7 is a graph showing the methylation frequency (mean value) of the $29^{th}$ to $31^{st}$ CpG sequences counted from the 5'-side in the peripheral region of the promoter of the Zar1 gene in each of 16 types of human-derived samples.
Figure 8:
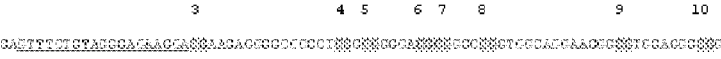
FIG. 8 is a view showing the peripheral region of the promoter of a human Zar1 gene (SEQ ID NO: 3).

Among mammals, humans have a CpG island having 187 CpG sequences in the peripheral region (SEQ ID NO: 3) of the promoter of a Zar1 gene (from the numbers 1 to 187 in FIG. 8). Among such 187 CpG sequences, the $29^{th}$ to $31^{st}$ CpG sequences counted from the 5'-side (the numbers 29 to 31 in FIG. 8) exist in a site to which a transcription control factor E2F binds. In this site, the demethylation of both cancer cells and normal cells is observed (FIG. 7, and E2F in FIG. 8). On the other hand, among such 187 CpG sequences, particularly in the $60^{th}$ to $187^{th}$ CpG sequences counted from the 5'-side, methylation is observed in cancer cells at a frequency significantly higher than that in normal cells (FIG. 6). In a case in which a biological sample is derived from a human, a sequence in the peripheral region of the promoter of the Zar1 gene, as described below, can be a target, in which methylation is to be detected by the method of the present invention:

(1) at least one CpG sequence;
(2) at least one CpG sequence selected from among CpG sequences other than the CpG sequences in the binding site of the transcription control factor E2F, and specifically, at least one CpG sequence selected from among CpG sequences other than the $29^{th}$ to $31^{st}$ CpG sequences counted from the 5'-side; or
(3) at least one CpG sequence selected from among the $60^{th}$ to $187^{th}$ CpG sequences counted from the 5'-side, for example, at least one CpG sequence selected from among the $118^{th}$ to $166^{th}$ CpG sequences counted from the 5'-side.

Further, among mammals other than humans, mice have a CpG island in the peripheral region of the promoter of a Zar1 gene (a region ranging from 56 bp upstream to 794 bp downstream of the transcription initiation point of the Zar1 gene), and 89 CpG sequences are present in such CpG island. The sequence of the site, to which the Zar1 transcription control factor E2F binds in humans, is highly conserved also in mice. The concerned site is present in a CpG island (which is peripheral to mouse chr5: 72, 972, 271-72, 972, 300). Furthermore, in rats as well, such sequence is highly conserved. Hence, it is predicted that the sequence of the site to which the Zar1 transcription control factor E2F binds will also be highly conserved in other mammals including dogs and horses.

Herein, in a case in which a CpG sequence used as a target for detecting methylation is selected from the genomic DNA of a Zar1 gene, such CpG sequence can be selected as follows, for example.

For instance, a CpG island is searched in the genomic DNA of a Zar1 gene as follows. A CpG island can be identified by searching it in the gene region using a genome browser (e.g. http://genome.ucsc.edu/), based on the conditions that such CpG island is a region having a length of at least 200 base pairs and having a GC content of 50% or more, in which the abundance of CpG is 60% or more greater than the predicted amount (the actual number of CpGs/the predicted number of CpGs in any given number of nucleotides can be calculated by the formula (the actual number of CpGs/the number of C×the number of G)×the number of nucleotides). For example, if the region of a human ZAR1 gene is searched with the genome browser under the above-described conditions, only a single CpG island can be identified as CpG: 187 in the ZAR1 gene region. More specifically, the nucleotide sequence of the CpG island CpG: 187 of the ZAR1 gene can be displayed as a region ranging from 48186875 to 48188346 on chromosome No. 4 on the aforementioned genome browser (http://genome.ucsc.edu/), and the sequence of the CpG island of the ZAR1 gene can be easily obtained therefrom. The CpG island (the region ranging from 48186875 to 48188346 on the chromosome No. 4) of the ZAR1 gene comprises 187 CpG sequences. Hence, individual numbers 1 to 187 are each assigned to the 187 CpG sequences, so that individual CpG sequences shown in FIG. 8 can be identified.

From the thus found region, at least one CpG sequence can be selected as a CpG sequence used as a target for detecting methylation.

Herein, the "at least one CpG sequence" means any number of one to all CpG sequences selected from the CpG sequences existing in the peripheral region of the promoter of the Zar1 gene. In the case of humans, such "at least one CpG sequence" is any number of 1 to 187 CpG sequences selected from the $1^{st}$ to $187^{th}$ CpG sequences shown in FIG. 8. It is, for example, any number of, 20 to 150, 30 to 140, or 40 to 130 CpG sequences. More specifically, it is 1, 10, 20, 30, 40, 50, 60, 70, 80, 90, 100, 110, 120, 130, 140, 150, 160, 170, 180, or 187 CpG sequences.

Moreover, the "at least one CpG sequence selected from among CpG sequences other than the CpG sequences in the binding site of the transcription control factor E2F" means any number of one to all CpG sequences other than the CpG sequences in the binding site of the transcription control factor E2F, which exist in the peripheral region of the promoter of the Zar1 gene. In the case of humans, such "at least one CpG sequence" is herein used to mean any number of 1 to 184 CpG sequences. It is, for example, any number of, 20 to 150, 30 to 140, or 40 to 130 CpG sequences. More specifically, it is 1, 10, 20, 30, 40, 50, 60, 70, 80, 90, 100, 110, 120, 130, 140, 150, 160, 170, 180, or 184 CpG sequences.

As described above, in the case of humans, methylation is observed particularly in the $60^{th}$ to $187^{th}$ CpG sequences counted from the 5'-side in cancer cells, at a frequency significantly higher than that in normal cells (FIG. 6). Thus, it is considered that the region of the $60^{th}$ to $187^{th}$ CpG sequences counted from the 5'-side particularly serves as an insulator to control the action of an enhancer. It had been known that a transcription control factor CCCTC binding factor (CTCF) binds to the insulator region of a vertebrate animal. The present inventors have confirmed that a site to which the CTCF probably binds is particularly present in the region of the $60^{th}$ to $187^{th}$ CpG sequence counted from the 5'-side. This putative CTCF-binding site is methylated at a high frequency in cancer cells. From this fact, it is assumed that the transcription control factor CTCF cannot bind to the insulator region in cancer cells, and that the methylated portion cannot act as an insulator, so that the enhancer activates the transcription control factor of ZAR1, and so that the ZAR1 can be expressed.

3. DETECTION OF METHYLATION

In order to detect of the methylation of the genomic DNA of a Zar1 gene, DNA is first extracted from a biological sample, using a commercially available DNA extraction kit or the like. Then, the extracted DNA is used for the detection of methylation.

A method for detecting the methylation of the genomic DNA of a Zar1 gene is not particularly limited, and a known method can be applied. Such methylation detection methods include: a method (MALDI-TOF MS) which utilizes a Matrix Assisted Laser Desorption/Ionization (MALDI) method and time-of-flight mass spectrometry (TOFMS); a Bisulfite Direct Sequence method; a Methylation Specific PCR method; and a Combined bisulfite-restriction analysis (COBRA) method.

More specifically, in the MALDI-TOF MS, the methylation of a CpG sequence is detected as follows. When cytosine (C) in DNA is treated with bisulfite, it is converted to uracil (U). However, methylated cytosine is not converted, but it remains as the methylated cytosine. Thus, if PCR is carried out using the bisulfite-treated DNA as a template, a methylated cytosine portion is converted to cytosine (C), and a non-methylated cytosine portion is converted to thymine (T). If this PCR product is transcribed to RNA, C is transcribed to guanine (G) and T is transcribed to adenine (A). If this RNA is digested by nucleotide-specific enzymes and is then analyzed by MALDI-TOF MS, methylation can be distinguished from non-methylation because G differs from A by a mass of 16 Da.

In the Bisulfite Direct Sequence method, the methylation of a CpG sequence is detected as follows. When cytosine (C) in DNA is treated with bisulfite, it is converted to uracil (U). However, methylated cytosine is not converted, but it remains as the methylated cytosine. Thus, if PCR amplification is carried out using the bisulfite-treated DNA as a template and the nucleotide sequence of the amplification product is then analyzed, a methylated cytosine portion can be distinguished as cytosine (C) and a non-methylated cytosine portion can be distinguished as thymine (T).

The nucleotide sequence of the amplification product can be analyzed by designing PCR primers that are irrelevant to methylation and non-methylation after completion of the bisulfite treatment and then applying the PCR method using the primers, or by performing mass spectrometry on a fragment of the sequence, or by utilizing restriction enzyme cleavage specific for a methylated or non-methylated sequence after completion of the bisulfite treatment, or the like.

Specifically, primers for amplifying CpG sequence(s) existing in a CpG island in the peripheral region of the promoter of a Zar1 gene after completion of the bisulfite treatment can be designed, for example, by placing the sequences in the program on the internet, MethPrimer (http://www.urogene.org/methprimer/index1.html). The nucleotide sequence of the amplification product can be determined using, for example, a sequencer of ABI, or a mass spectrometer MassArray of Sequenome. The presence or absence of the methylation of a CpG island in the peripheral region of the promoter of the Zar1 gene can be determined by comparing the thus determined nucleotide sequence of the amplification product with the nucleotide sequence of the genomic DNA before performing the bisulfite treatment.

For instance, as described later, humans have a region, in which the methylation frequency of the 127 CpGs existing in the $60^{th}$ to $187^{th}$ CpG sequences counted from the 5'-side is significantly different between in cancer cells and in normal cells. As primers for amplifying a portion of this region, the following primers can be designed, for example.

```
Primer 1:
5'-TTTGGAGTAGGGTAGTTTTTAGAA      (SEQ ID NO: 10)

Primer 2:
5'-CCCCCTCCTCTAAACCTTAAAA       (SEQ ID NO: 11)
```

Using these primers, a Bisulfite Direct Sequence method can be performed.

In the Methylation Specific PCR method (MSP method), the methylation of CpG sequences is detected as follows. As with the above-described Bisulfite Direct Sequence method, when cytosine (C) in DNA is treated with bisulfite, it is converted to uracil (U). However, a methylated cytosine is not converted, but it remains as the methylated cytosine. Thus, using the bisulfite-treated DNA as a template, PCR primers that are specific for methylation and demethylation can be designed. In the MSP method, the bisulfite-treated DNA is distinguished by methylation-specific and demethylation-specific PCR, and is then amplified. Thereafter, each DNA amount is determined.

In the Combined bisulfite-restriction analysis (COBRA) method, the methylation of CpG sequences in the peripheral region of a promoter is detected as follows. As with the Bisulfite Direct Sequence method, DNA is treated with bisulfite, and is then subjected to PCR. When a PCR product is cleaved by restriction enzymes specific for CpG sequence, a methylated DNA-derived PCR product is cleaved by the restriction enzymes, whereas a non-methylated DNA-derived PCR product is not cleaved by the restriction enzymes. Thus, when the PCR products are subjected to electrophoresis after completion of the cleavage by the restriction enzymes, a difference is observed in bands, and as a result, methylation can be distinguished from non-methylation.

It is to be noted that the details of the MALDI-TOF MS and the Bisulfite Direct Sequence method will be described in Examples. The Methylation Specific PCR method is described, for example, in Herman J G and Baylin S B Methylation Specific PCR, in Current Protocol in Human Genetics, 1998. The COBRA method is described, for example, in Xiong Z & Laird P W: Nucleic Acids Res 25: 2529-2531, 1997.

When the frequency of the methylation of genomic DNA (e.g. the methylation of CpG sequences) as detected above is higher than the frequency of the methylation of the corresponding genomic DNA (e.g. the methylation of CpG sequences) in normal cells, it can be determined that the concerned biological sample is affected with proliferative disease. For example, it can be determined that the biological sample has become cancerous. More specifically, when the frequency of the methylation of genomic DNA (e.g. the methylation of CpG sequences) is higher than the frequency of the methylation of the corresponding genomic DNA (e.g. the methylation of CpG sequences) in normal cells, and/or when the methylation frequency is 50% or more, 60% or more, 70% or more, 80% or more, or 90% or more; and preferably, when the frequency of the methylation of genomic DNA (e.g. the methylation of CpG sequences) is higher than the frequency of the methylation of the corresponding genomic DNA (e.g. the methylation of CpG sequences) in normal cells, and when the methylation frequency is 50% or more, 60% or more, 70% or more, 80% or more, or 90% or more, it can be determined that the biological sample is affected with proliferative disease, for example, it is a biological sample derived from the affected area of a patient with proliferative disease, or the biological sample has become cancerous.

Herein, in the present invention, as described above, when the methylation frequency of a certain patient is 50% or more, 60% or more, 70% or more, 80% or more, or 90% or more, it can be determined that the probability that the patient is affected with proliferative disease is 40% or more, 50% or more, 60% or more, 70% or more, 80% or more, 90% or more, or 100%.

The reference value F % of methylation frequency indicating, for example, that the probability of proliferative disease is P % may be adjusted by accumulating cases. The type of statistical processing used to adjust such reference value F % of methylation frequency is not particularly limited. A method known in the present field may be applied.

Herein "the methylation frequency of genomic DNA" means the percentage (%) of methylated cytosine, guanine, adenine and thymine in DNA in the genome. In addition, "the methylation frequency of CpG sequences" means the percentage (%) of methylated cytosines in the cytosines in CpG sequences.

Such frequency can be expressed with numbers from 0% to 100%. For example, when cytosine is methylated in a single CpG sequence, the methylation frequency of the CpG sequence is 100%. On the other hand, when cytosine is demethylated in a single CpG sequence, the methylation frequency of the CpG sequence is 0%. As for the methylation frequency of CpG sequences, when the methylation frequency of two or more CpG sequences is obtained, the methylation frequencies of individual CpG sequences may be added up, and the total value may be then divided by the number of the CpG sequences to obtain a mean value. That is to say, when a Y (Y≧1) number of CpG sequences is methylated in an X (X≧2) number of CpG sequences in a certain region, the methylation frequency Z % of the CpG sequences in this region can be obtained by the formula: Z(%)=[100%×Y (number)]/X (number).

Moreover, the methylation frequency of the above-described single CpG sequence, or the methylation frequency of the above-described two or more CpG sequences, may be a mean value of the methylation frequencies obtained by two or more measurements. Specifically, in an n (n≧2) number of measurements, when the methylation frequency in the $i^{th}$ (i=1, 2, . . . , n) measurement is Zi %, the methylation frequency Z % can be obtained by the formula: Z(%)=[Z1(%)+Z2(%)+ . . . +Zi(%)+ . . . +Zn(%)]/n (number).

For example, the "methylation frequency of CpG sequences" is indicated by color density in FIGS. 2, 9, 11, and 13. This is a value obtained by measuring the methylation frequency of each of the $118^{th}$ to $166^{th}$ CpG sequences counted from the 5'-side in the peripheral region of the promoter of a Zar1 gene in the biological sample derived from a human, and then averaging the measurement value by three measurements.

Moreover, the longitudinal axis in each of FIGS. 4, 5, 10, 12 and 14 indicates the "methylation frequency of CpG sequences." This is a value obtained by measuring the methylation frequency of each of the $118^{th}$ to $166^{th}$ CpG sequences counted from the 5'-side in the peripheral region of the promoter of a Zar1 gene in the biological sample derived from a human, then adding up the measurement values of the CpG sequences, then dividing the total value by the number of the $118^{th}$ to $166^{th}$ CpG sequences (49) to obtain a mean value, and then averaging this mean value by three measurements.

In the present invention, the thus detected methylation is used as a marker, so as to detect cancer in a biological sample. When the final diagnosis is made, the detection results obtained using other markers, the examination results of roentgenologic examination, CT, MRI, etc., and other results may be combined with the detection results obtained using the marker of the present invention, so that the results may be comprehensively analyzed and the final diagnosis may be made regarding proliferative disease such as cancer. Hence, the diagnosis of proliferative disease such as cancer can be more precisely made by combining a plurality of detection results and examination results, such as the detection results of proliferative disease such as cancer, which are obtained using the marker of the present invention and other markers, and the examination results obtained by roentgenologic examination, CT, MRI, etc.

4. BIOLOGICAL SAMPLE

In the present invention, the biological sample used for the detection or diagnosis of cancer is derived from mammals. Examples of such mammals include humans, mice, rats, horses, bovines, sheep, monkeys, dogs and cats. Among them, humans are preferable.

The "biological sample" is used herein to mean cells or tissues derived from mammals. The biological sample may be obtained either by biopsy or by collection of blood. Thus, the method of obtaining the biological sample is not particularly limited. It is to be noted that, since the Zar1 gene is expressed specifically in egg cells in the ovary, such egg cells are excluded from the biological sample in a preferred embodiment of the present invention.

In the present invention, proliferative disease-derived DNA existing in such biological sample is detected.

The "proliferative disease (cellular proliferative disease)" includes diseases attended with cell proliferation. The specific type of such "proliferative disease" is not particularly limited. An example of the proliferative disease is at least one selected from the group consisting of tumor (e.g. cancer), benign prostatic hypertrophy, and hydatid mole. A particular example is cancer.

The type of such "cancer" is not particularly limited. An example of the cancer is at least one selected from the group consisting of malignant melanoma, esophageal cancer, neuroblastoma, glioblastoma, glioma, Wilms tumor, cutaneous squamous cell carcinoma, lung adenocarcinoma, lung squamous cell carcinoma, breast cancer, osteosarcoma, rhabdosarcoma, pancreatic cancer, colon cancer, renal cell carcinoma, prostatic cancer, urothelial carcinoma, bladder cancer, cervical cancer, squamous cell carcinoma of the tongue, hepatoblastoma, malignant lymphoma, pharyngeal cancer, laryngeal cancer, stomach cancer, liver cancer, angioma, thyroid cancer, testicular tumor, digestive system cancer, cancer of upper jaw, cancer of tongue, cancer of lip, oral cavity cancer, gallbladder cancer, cholangioma, biliary tract cancer, rectal cancer, ureteral tumor, brain tumor, leukemia, and ovarian cancer. A particular example is at least one selected from the group consisting of malignant melanoma, esophageal cancer, neuroblastoma, glioblastoma, glioma, Wilms tumor, cutaneous squamous cell carcinoma, lung adenocarcinoma, lung squamous cell carcinoma, breast cancer, osteosarcoma, rhabdosarcoma, pancreatic cancer, colon cancer, renal cell carcinoma, prostatic cancer, urothelial carcinoma, bladder cancer, cervical cancer, squamous cell carcinoma of the tongue, and hepatoblastoma. Further examples include malignant melanoma, neuroblastoma, hepatoblastoma, and bladder cancer.

The "normal cells" are used herein to mean cells in which proliferative disease is not detected, for example, cells which have not yet become cancerous.

Hereinafter, the present invention will be more specifically described in the following examples. However, these examples are not intended to limit the scope of the present invention.

EXAMPLES

Example 1

1. Biological Sample

The following biological samples were used: 30 cases of malignant melanoma patient specimens, which were examined and were subjected to surgery at Dermatological Section, Itabashi Hospital, Nihon University School of Medicine and which were histopathologically diagnosed as malignant melanoma (10 cases of cryopreserved specimens and 20 cases of paraffin-embedded specimens); 17 types of malignant melanoma cell lines; 4 types of normal human skin melanocyte cell lines; 3 cases of normal human ovary excised at Gynecological Section, Itabashi Hospital, Nihon University School of Medicine (paraffin-embedded specimens); 1 type of normal human umbilical vein vascular endothelial cell line; 63 types of other malignant tumor cell lines; and 3 types of normal human fibroblast cell lines.

Specimens were collected from patients, after the patients had been explained about specimen collection and written informed consent had been then obtained from all the patients. In addition, the present experiment was approved by the ethics committee of Nihon University School of Medicine and the ethics committee of Itabashi Hospital, Nihon University School of Medicine.

Among the malignant melanoma cell lines, G-361, COLO679, CRL1579 and SK-MEL-28 were purchased from RIKEN BioResource Center (Tsukuba-shi, Ibaraki); GAK, MeWo, A2058 and HMY-1 were purchased from Health Science Research Resources Bank (Sennan-shi, Osaka); and SK-MEL-2, SK-MEL-31, RPMI-7951, A375, COLO829, HT144, Hs294T, Hs695T and Hs839T were purchased from American Type Culture Collection (Virginia, U.S.A.).

The normal human melanocyte cell lines NHEM-L, NHEM-M, NHEM-D and HEMa-LP, and the normal human umbilical vein vascular endothelial cell line HUVEC were purchased from Cascade Biologics (Oregon, U.S.A.).

Other malignant tumor cell lines TE1, TE2, TE3, TE4, TE5, TE7, TE8, TE9, TE11, TE12, TE13, TE15, KE3, KE6 and KE8 (esophageal cancer), SK-N-D2, SK-N-SH, CHP134, NBLS and KELLY (neuroblastoma), U373, A172 and U118 (glioblastoma), U251 and HS683 (glioma), GOS4 (Wilms tumor), A431 (cutaneous squamous cell carcinoma), NCI-H441 (lung adenocarcinoma), SK-MES-1 (lung squamous cell carcinoma), MCF7 and MDA-MB-231 (breast cancer), SAOS and U205 (osteosarcoma), JR-1 (rhabdosarcoma), ASPC and BXPC3 (pancreatic cancer), RKO, LOVO, COLO205, LS180, SW620, SW480, HT29 and HCT116 (colon cancer), RCC (renal cell carcinoma), PC3, 22RV, LNCAP and DU145 (prostatic cancer), J82 (urothelial carcinoma), T24 (bladder cancer), HeLa-TR (cervical cancer), TR126 (squamous cell carcinoma of the tongue), and QMHK11, QMHK10, VIAMM7, 4785A, 4785C, 4785D, VIAMM2, 6547, 6547A, 3576c1-A and 3576c1-B (unspecified cell lines) were acquired from the Roswell Park Cancer Institute (Buffalo, N.Y., U.S.A.).

Further, normal fibroblast cell lines MRC5p30, KMp15 and TSp28 were also acquired from the Roswell Park Cancer Institute (Buffalo, N.Y., U.S.A.).

2. Methods

Methods used in the present Examples will be described below.

(1) Restriction Landmark Genomic Scanning (RLGS) Method

Nucleotide analogs (αS-dGTP, αS-dCTP, ddATP and ddTTP) and 2 U DNA polymerase I were added to 1 to 3 μg of DNA obtained from mouse skin cancer (spinocellular carcinoma), liver cancer and lung cancer, to a total amount of 10 μl. Thereafter, the mixture was blocked by performing reactions at 37° C. for 20 minutes and at 65° C. for 30 minutes.

Subsequently, the pH of a buffer was adjusted, and 20 U NotI (Promega) was then added to 10 μl of the sample, followed by a reaction at 37° C. for 2 hours, so that the first DNA cleavage was carried out.

Thereafter, [α-32P]dGTP and [α-32P]dCTP were added to the resultant, and the mixture was reacted at 37° C. for 30 minutes using Sequenase (version 2.0, U.S.B.), so as to perform labeling. The labeled DNA was reacted at 37° C. for 1 hour using 20U PstI, so that the second DNA cleavage was carried out. Thereafter, electrophoresis was carried out using 0.8% agarose tube gel with a length of 60 cm (one-dimensional electrophoresis).

After completion of the one-dimensional electrophoresis, the agarose tube gel was placed in a PvuII buffer, and the obtained mixture was then reacted at 37° C. for 2 hours, so that the third DNA cleavage was carried out in the gel.

Agarose gel was horizontally positioned at the tip of 5% polyacrylamide gel (which was rotated 90 degrees from that in the one-dimensional electrophoresis), and the melted agarose was then allowed to absolutely come into contact with the polyacrylamide gel. Thereafter, two-dimensional electrophoresis was carried out.

After completion of the two-dimensional electrophoresis, the gel was dried, and autoradiogram was then carried out for 2 to 10 days using intensifying screen (QuantaIII, DuPont) as an X-ray film.

Each sample was analyzed in a triplicate manner.

(2) Extraction of DNA

Using a knife, approximately 20 to 30 mg of tumor cells were extracted from cryopreserved specimens. Thereafter, using QIAamp DNA mini kit (QIAGEN, Maryland, U.S.A.), DNA was extracted from the cells in accordance with protocols included with the kit.

In the case of paraffin-embedded specimens, the specimens were sliced to a thickness of 20 μm, and tumor portions were then extracted from the five sections using a knife. Thereafter, the tumor portions were subjected to a deparaffinization treatment with xylene at room temperature, and DNA was then extracted as in the case of the cryopreserved specimens.

In the case of cell lines, DNA was extracted from $5 \times 10^6$ cells, using QIAamp DNA mini kit.

With regard to the extraction of DNA from oocytes, normal human ovarian tissues embedded in paraffin were first sliced to a thickness of 5 μm, using a microtome. Thereafter, the sample was placed on a slide glass with foil (Leica Microsystems, Tokyo), and it was then subjected to deparaffinization and HE staining. Thirty slide glasses were prepared for a single sample. Subsequently, using Laser Microdissection System LMD6000 (Leica Microsystems), oocytes were cut in the form of single cells, and a total of 500 to 1000 cells were collected. Since the specimen is in a trace amount, 10 μl of (10 mg/ml) salmon sperm DNA (Invitrogen, California, U.S.A.) was added to 100 μl of buffer. The protein was decomposed with proteinase K (5 mg/ml), and DNA was then extracted with phenol/chloroform.

(3) Extraction of RNA

From each of the 17 types of malignant melanoma cell lines and the 4 types of normal human skin melanocyte cell lines, $5 \times 10^6$ cells were used. RNA was extracted from the cells, using QIA shredder (QIAGEN) and RNeasy Mini Kit (QIAGEN).

(4) Bisulfite Treatment

1 μg of the extracted DNA was treated with bisulfite, using EZ DNA methylation kit (Zymo Research, California, U.S.A.).

First, ultrapure water (Milli-Q) was added to 1 μg of the DNA to a total amount of 45 μl. The obtained mixture was reacted at 95° C. for 10 minutes, and immediately after completion of the reaction, the sample was placed on ice, so that it was quenched.

Subsequently, 5 μl of M-Dilution was added to the resultant, and the obtained mixture was then reacted at 37° C. for 15 minutes. Thereafter, 100 μl of CT Conversion Reagent was added to the reaction product, followed by 15 cycles of reaction at 95° C. for 30 seconds and at 50° C. for 15 minutes. Thereafter, the sample was purified in accordance with protocols, and the final extraction was then carried out using 50 μl of ultrapure water (Milli-Q).

(5) PCR

Primers used in PCR were designed using the METHPRIMER program (http://www.urogene.org/methprimer/index1.html) or Methyl Primer Express (registered trademark) Software v1.0 (Applied Biosystems, California, U.S.A.). All primers were purchased from Operon Biotechnologies (Itabashi, Tokyo). A tag of 5'-aggaagagag-3' (SEQ ID NO: 4) was added to each Forward primer, and a tag of 5'-cagtaatacgactcactatagggagaaggct-3' (SEQ TD NO: 5) was added to each Reverse primer.

Using HotStar Taq Polymerase (Qiagen), a PCR reaction was carried out with 1 μl of bisulfite-treated DNA. The PCR reaction was carried out using a 384-hole microtiter plate. The amount of the PCR reaction solution was set at 5 μl and HotStar Taq DNA Polymerase 1000 Units (QIAGN) was added thereto. The obtained mixture was heated at 94° C. for 15 minutes, and one cycle consisting of the following conditions was then repeated 45 times.

Heat denaturation: 94° C., 20 seconds;
Annealing: at an annealing temperature from 52° C. to 62° C. for each primer, for 45 seconds; and
An elongation reaction: 72° C., 1 minute.

Thereafter, the final elongation was carried out at 72° C. for 3 minutes.

(6) Dephosphorylation of Unreacted dNTP

2 μl of an enzyme reaction solution, 1.0 U/μl Shrimp Alkaline Phosphatase (SAP) Enzyme (SEQUENOM, California, U.S.A.), was added to 5 μl of the PCR reaction solution, and the obtained mixture was then reacted at 37° C. for 20 minutes and at 85° C. for 5 minutes, so that unreacted dNTP was dephosphorylated.

(7) Transcription into RNA and T(U)-Specific or C-Specific Cleavage Reaction Using RNaseA (Ribonuclease A)

A new 384-well microtiter plate was prepared. 2 µl of the SAP-treated reaction solution was added to total 5 µl of a mixed solution consisting of 3.15 µl of RNase Free ddH2O, 0.89 µl of 5×T & Polymerase Buffer, 0.24 µl of T or C Cleavage mix, 0.22 µl of DTT (100 mM), 0.44 µl of T7 RNA & DNA Polymerase and 0.06 µl of RNaseA (all of which were from Mass CLEAVE (registered trademark) Reagent Kit; SEQUENOM). The obtained mixture was reacted at 37° C. for 3 hours.

(8) Desalination with SpectroCLEAN

20 µl of ultrapure water (Milli-Q) was added to the reaction solution, and 6 mg of SpectroCLEAN (SEQUENOM) was then added thereto. The obtained mixture was incubated for 10 minutes, and was then centrifuged at 3200 g for 5 minutes.

(9) Sample Spotting

The desalinated reaction product was spotted onto SpectroCHIP (SEQUENOM), using a special nano spotter (SEQUENOM MassARRAY Nanodispenser).

(10) Measurement by Time-of-Flight Mass Spectrometer and Analysis of Methylation The thus spotted SpectroCHIP was subjected to a mass spectrometer, MassARRAY Analyzer Compact MALDI-TOF MS (Sequenom), so as to carry out accurate mass analysis. A Matrix Assisted Laser Desorption/Ionization method (MALDI method) was applied to the measurement. In this method, a sample that has been uniformly mixed with a large amount of matrix is allowed to absorb liquid nitrogen laser (wavelength: 337 nm) that is ultraviolet light, so that it is converted to thermal energy. During this step, only a part of the matrix (uppermost surface to 100 nm of the analyte) was rapidly (a few nsec) heated, and it is vaporized together with the sample. As a result of this phenomenon, cations of various sizes are generated on a sample slide, and the ions are drawn to the same direction due to potential difference. After completion of the drawing, each ion velocity v can be obtained according to the law of conservation of energy. Herein, since the potential difference V0 is constant to all the ions, the smaller (the lighter) the m/z value of the ion, the faster the ion flies across drift space to arrive a detector. Thus, quantitative accurate mass analysis was carried out by applying "time-of-flight mass spectrometry (TOFMS)," a method for conducting mass spectrometry utilizing a phenomenon whereby the flight times of ions differ depending on a difference in a mass-to-charge ratio, m/z value. The results were analyzed using EpiTYPER software v1.0 (Sequenom).

The presence or absence of methylation can be determined as follows. If PCR is carried out using the bisulfite-treated DNA as a template, a methylated cytosine portion is converted to cytosine (C), and a non-methylated cytosine portion is converted to thymine (T). If this PCR product is transcribed to RNA, C is transcribed to guanine (G) and T is transcribed to adenine (A). If this RNA is digested by nucleotide-specific enzymes and is then analyzed by MALDI-TOF MS, methylation can be distinguished from non-methylation because G differs from A by a mass of 16 Da.

(11) Analysis by Bisulfite Direct Sequence Method

The bisulfite-treated DNA was analyzed using Applied Biosystems 3100x1 Genetic Analyzer (Applied Biosystems) and also using BioDye (registered trademark) Terminator v3.1 Cycle Sequencing kit in accordance with protocols (StdSeq50_POP7_v1).

The presence or absence of methylation can be determined as follows. When cytosine (C) in DNA is treated with bisulfite, it is converted to uracil (U). However, methylated cytosine is not converted, but it remains as the methylated cytosine. Thus, if PCR amplification is carried out using the bisulfite-treated DNA as a template and the nucleotide sequence of the amplification product is then analyzed, a methylated cytosine portion can be distinguished as cytosine (C) and a non-methylated cytosine portion can be distinguished as thymine (T). Thereby, the presence or absence of methylation can be determined.

(12) Gene Expression Analysis by Real-Time RT-PCR (Reverse Transcription Polymerase Chain Reaction)

500 ng of the extracted RNA was subjected to a reverse transcription reaction using Prime Script RT Reagent Kit (Takara Bio Inc., Shiga, Japan), so as to synthesize a complementary DNA strand, cDNA.

Real-time RT-PCR was carried out employing SYBR Premix Ex Taq (Takara Bio Inc.) and using Thermal Cycler Dice (registered trademark) Real Time System (Takara Bio Inc.). Primers used herein were purchased from Takara Bio Inc. The sequences of the primers and the applied annealing temperature are as follows.

```
Primer sequences:
HA062862-F:
5'-AATATGGCTATTACCACTGCAAGGA;     (SEQ ID NO: 6)
and

HA062862-R:
5'-GGCAGGAACATCTCGTTTGTTTA.       (SEQ ID NO: 7)
```

Annealing temperature: 62° C.

GAPDH was used as an internal standard gene. Primers for GAPDH were designed using Primer3 (http://biotools.umassmed.edu/bioapps/primer3_www.cgi). The used primers were purchased from Operon Biotechnologies (Itabashi, Tokyo). The sequences of the primers and the applied annealing temperature are as follows.

```
Primer sequences:
GAPDH-F
5'-GCACCGTCAAGGCTGAGAAC-3';       (SEQ ID NO: 8)
and

GAPDH-R
5'-TGGTGAAGACGCCAGTGGA-3'.        (SEQ ID NO: 9)
```

Annealing temperature: 62° C.

25 µl of a two-step RT-PCR mixture consists of 12.5 µl of SYBR Premix Ex Taq, forward and reverse primers (0.5 µl each), 10.5 µl of RNase-free water, and 1 µl of template cDNA. The reaction was carried out in a reaction system having real-time cycle conditions of 95° C., 10 seconds, 95° C., 5 seconds, and 60° C., 30 seconds. The amount of a Zar1 gene was standardized by comparing it with the expression level of GAPDH.

Each sample was subjected to relative quantitative analysis in a triplicate manner. The obtained data was analyzed using Microsoft EXCEL (registered trademark).

3. Results 15 mouse skin cancer-specific methylated portions, 8 mouse liver cancer-specific methylated portions, and 4 mouse lung cancer-specific methylated portions were identified according to an RLGS method. Thereafter, human gene regions corresponding to the thus identified mouse gene regions (27 portions) were searched through University of California, Santa Cruz (UCSC), Bioinfomatics Database (http://genome.ucsc.edu/). As for mice, searching was carried out using Mouse August 2005 assembly. As for humans, searching was carried out using Human March 2006 assembly.

Primers were designed with respect to the human gene regions obtained as a result of the searching. First, 10 cases of cryopreserved malignant melanoma specimens, 17 types of malignant melanoma cell lines, and 3 types of normal human skin melanocyte cell lines were measured using a mass spectrometer, MassARRAY Analyzer Compact MALDI-TOF MS (hereinafter referred to as MassARRAY). The measurement results were analyzed using EpiTYPER software v1.0.

Figure 1:
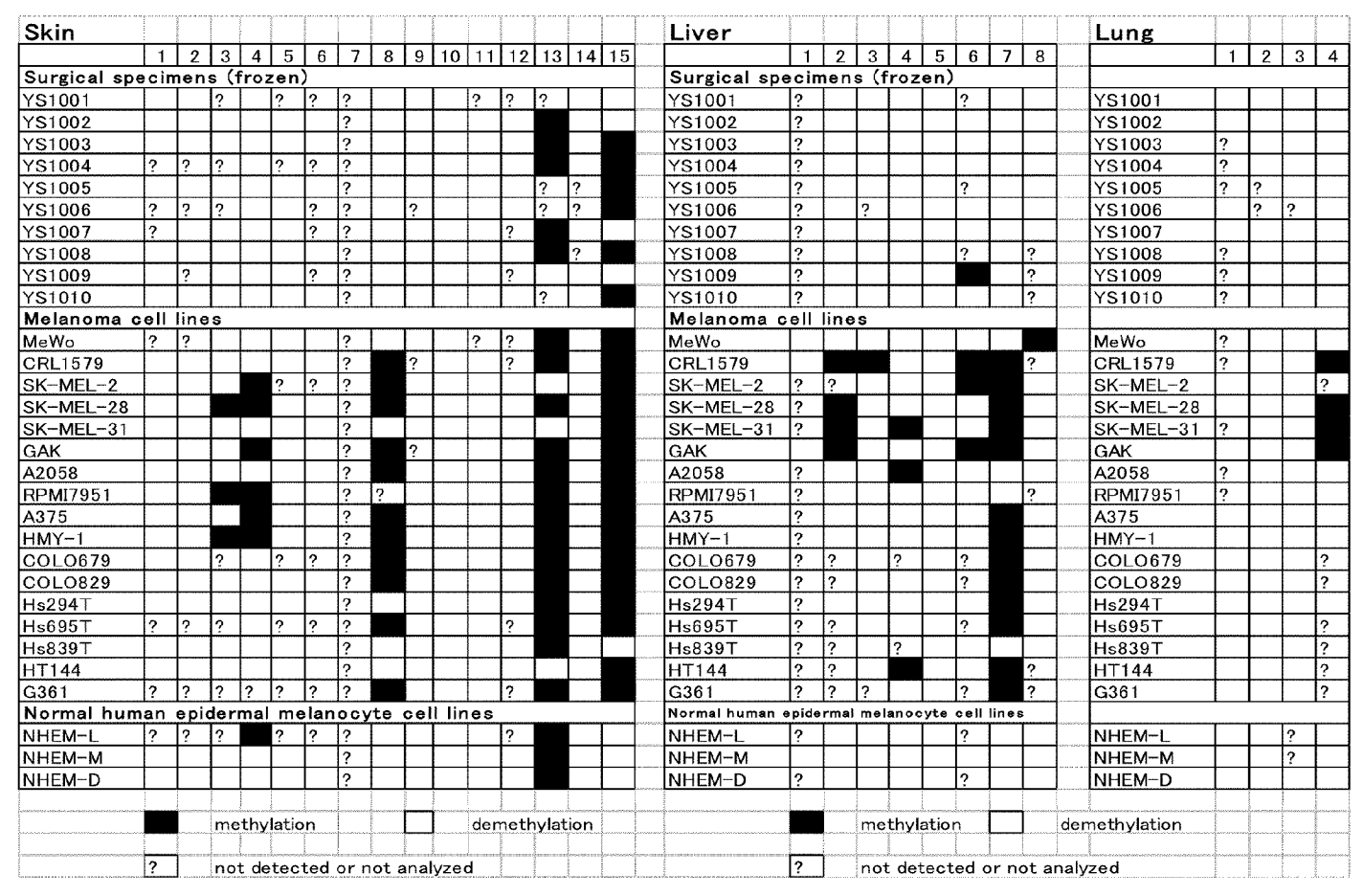

The analytical results are shown in FIGS. 1 and 2.

FIG. 1 is a view showing the results obtained by analyzing 30 types of human-derived samples, in terms of the presence or absence of methylation in the 27 gene regions thereof. In FIG. 1, the methylation frequencies of CpG sequences contained in individual PCR products were added up. When the mean value obtained by dividing the obtained methylation frequency by the number of the CpG sequences was 50% or more, it was determined that methylation was observed. Likewise, when the above mean value was 50% or less, it was determined that demethylation was observed. In the FIG. 1, the symbol "?" means that measurement or analysis has not yet been performed (not detected or not analyzed).

FIG. 2 is a view showing the details of the results obtained by analyzing Skin 15 of FIG. 1, in terms of the presence or absence of methylation. Among 187 CpG sequences existing in the peripheral region of the promoter of Skin 15, the methylation of the $118^{th}$ to $166^{th}$ CpG sequences counted from the 5'-side was analyzed.

With regard to one out of the analyzed 27 genes (Skin 15 of FIG. 1), methylation was observed in 6 out of the 10 patient specimens and in 16 out of the 17 types of malignant melanoma cell lines, and demethylation was observed in all the 3 types of normal human skin melanocyte cell lines.

This gene is Zygote Arrest 1 (Zar1). It has been reported that the Zar1 gene is specifically expressed in the human ovary, and that it plays an important role for the development of individuals (Wu X et al. Nat Genet 33: 187-91, 2003). To date, it has not been reported that the methylation of the Zar1 gene is associated with the development of cancer. The region that has been searched in the present study is a region, in which CpG118 to CpG166 (the $118^{th}$ to 166 CpG sequences counted from the 5'-side) located downstream of the binding site of the transcription control factor E2F are present, in the CpG sequences (the number of CpGs: 187) existing in the peripheral region of the promoter of Zar1.

Furthermore, 2 cases of patient specimens, 4 types of malignant melanoma cell lines, and 2 types of normal human skin melanocyte cell lines were analyzed also by the Bisulfite Direct Sequence method, and the same results were obtained.

Figure 3:
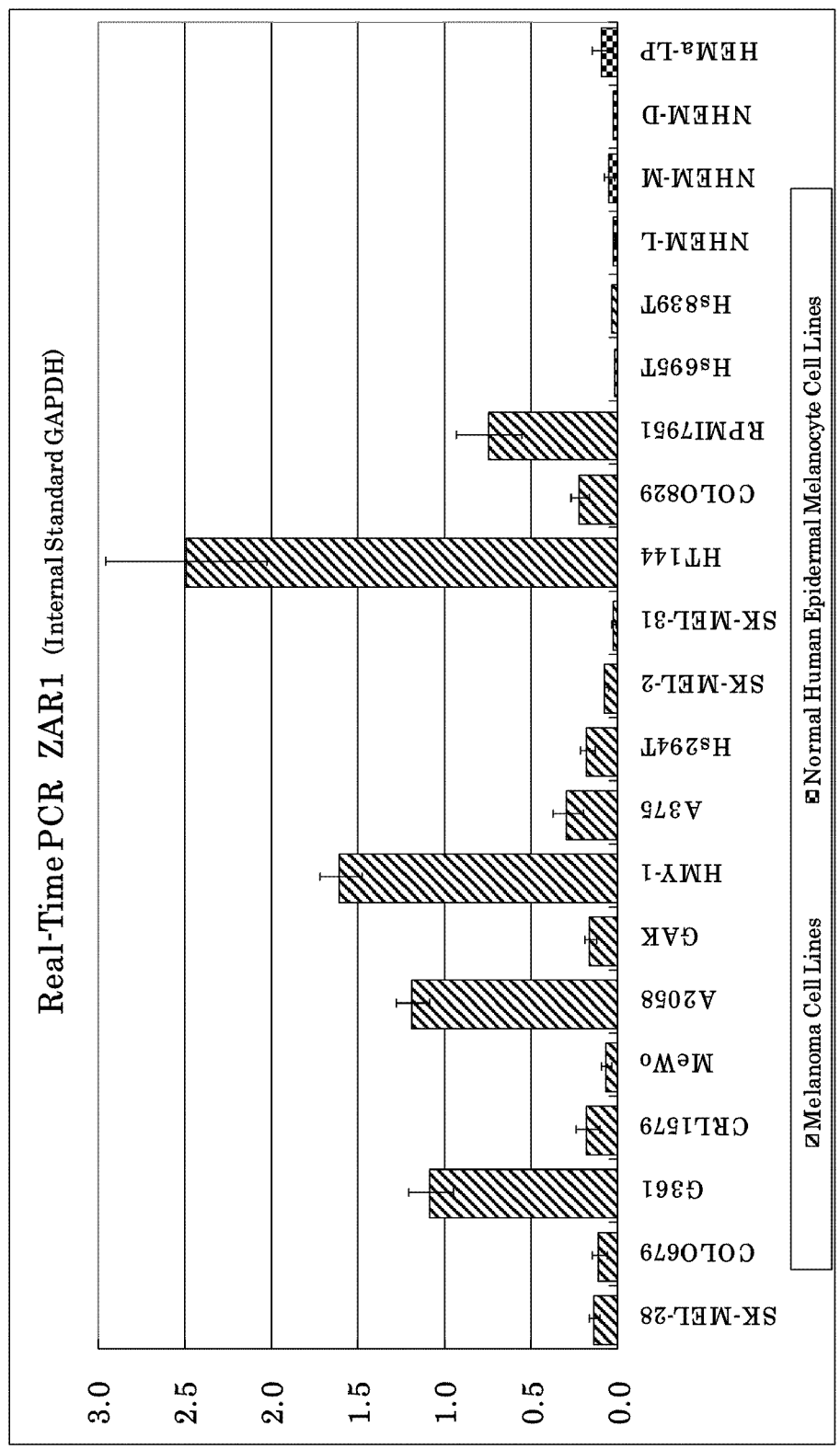
FIG. 3 is a graph showing the results obtained by analyzing 21 types of human-derived samples by real-time RT-PCR, in terms of the expression of the Zar1 gene.

Subsequently, according to real-time RT-PCR, gene expression analyses were performed on 17 types of malignant melanoma cell lines and 4 types of normal human skin melanocyte cell lines. A clear increase in the expression of the Zar1 gene was observed in 5 types of malignant melanoma cell lines (G-361, A2058, HMY-1, HT144 and RPMI7951), in which the peripheral region of the promoter of Zar1 had been methylated. In contrast, such increase in the expression was not observed in the 4 types of normal human skin melanocyte cell lines, in which the peripheral region of the promoter of Zar1 had been demethylated. The results are shown in FIG. 3.

Figure 4:
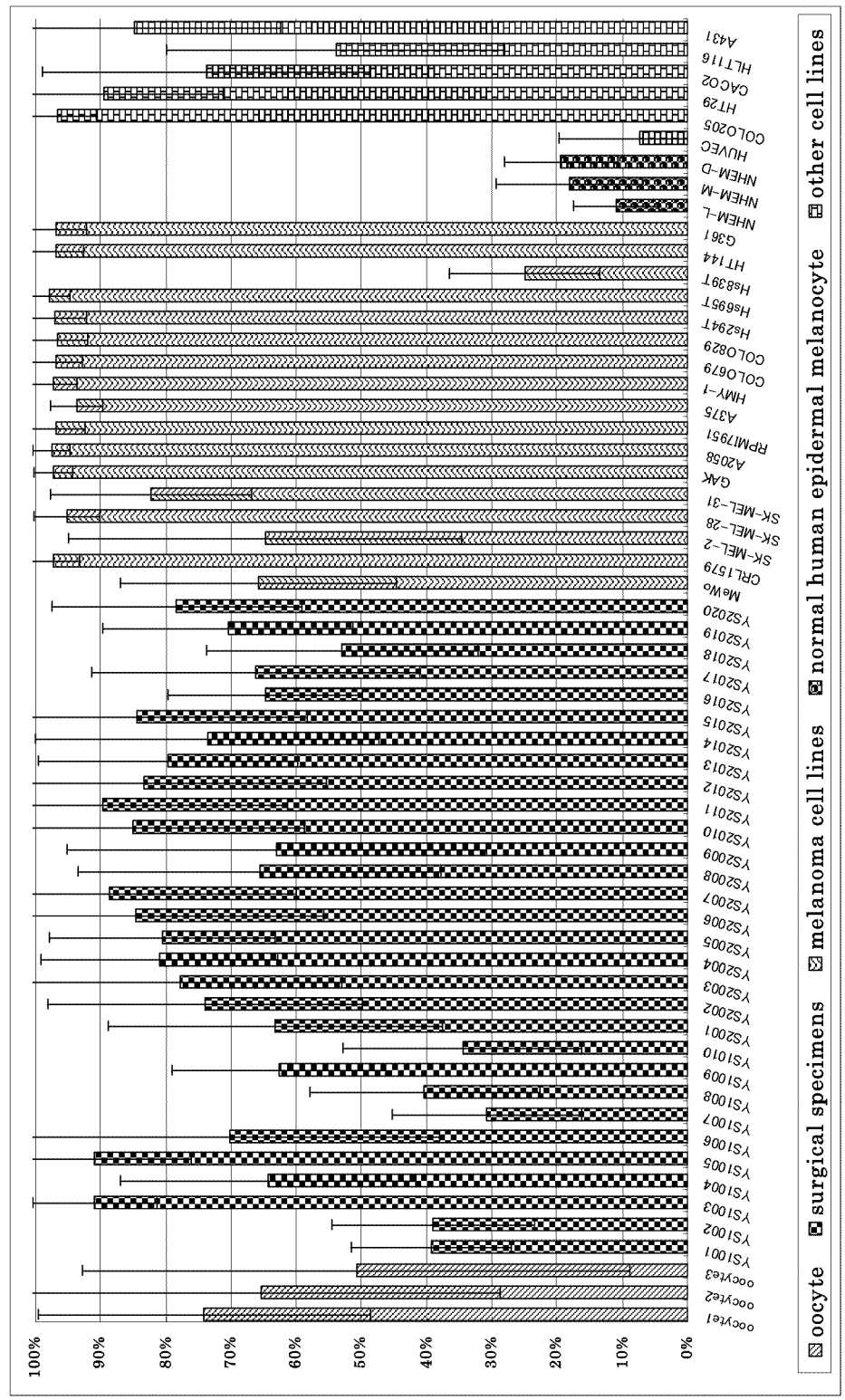
FIG. 4 is a graph showing the methylation frequency (mean value) of the $118^{th}$ to $166^{th}$ CpG sequences counted from the 5'-side in the peripheral region of the promoter of the Zar1 gene in each of 59 types of human-derived samples.
Figure 5:
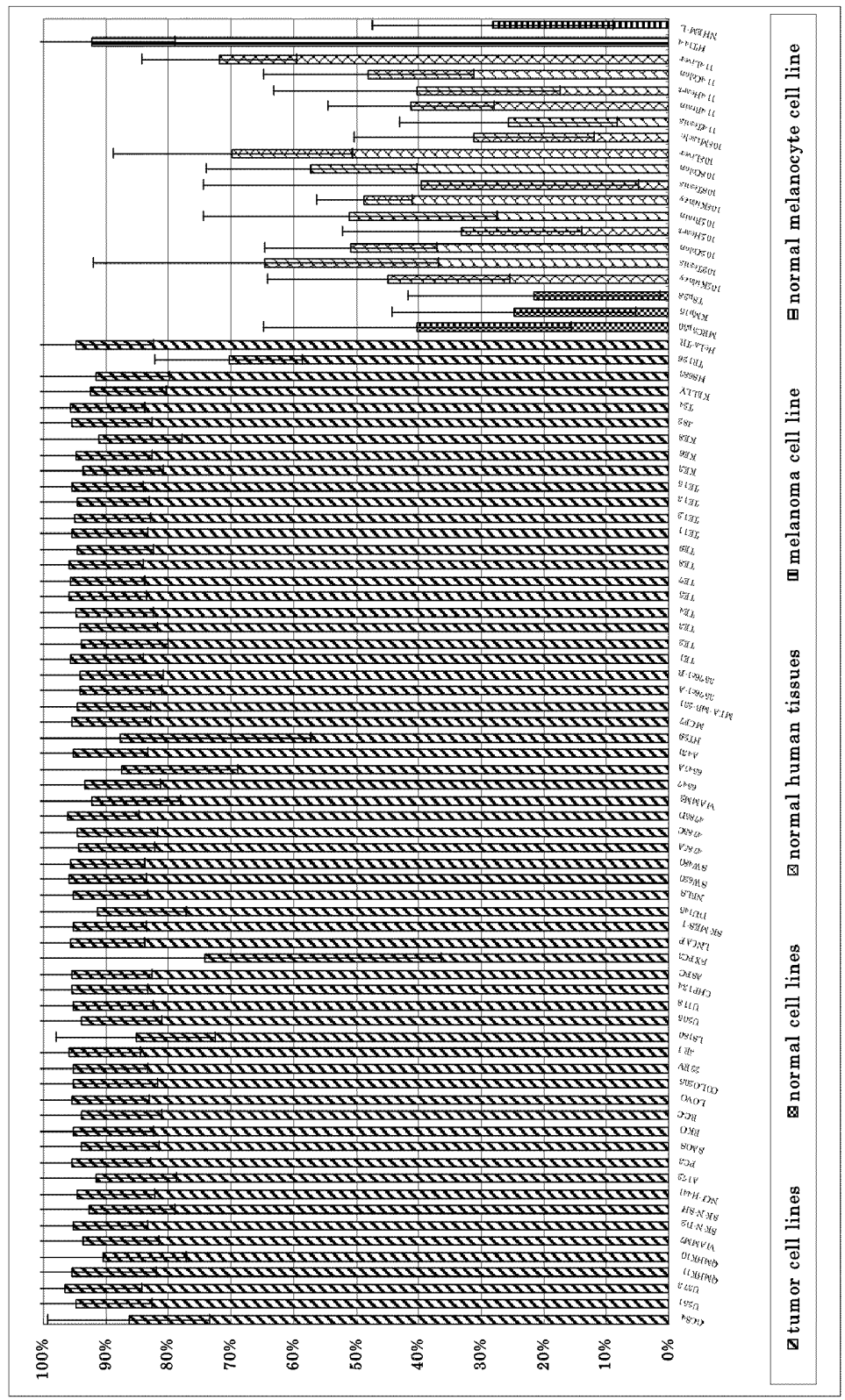
FIG. 5 is a graph showing the methylation frequency (mean value) of the $118^{th}$ to $166^{th}$ CpG sequences counted from the 5'-side in the peripheral region of the promoter of the Zar1 gene in each of 42 types of human-derived samples.

Thereafter, the remaining malignant melanoma patient specimens (20 cases of paraffin-embedded specimens), cell lines other than such malignant melanoma cell lines (1 type of normal human umbilical vein vascular endothelial cell line, 63 types of malignant tumor cell lines, and 3 types of normal human fibroblast cell lines), and oocytes were also examined using MassArray. As a result, methylation was observed in the peripheral region of the promoter of the Zar1 gene in all of such malignant melanoma patient specimens, malignant tumor cell lines and oocytes. On the other hand, demethylation was observed in the normal human umbilical vein vascular endothelial cell line and the normal human fibroblast cell lines. The results are shown in FIGS. 4 and 5. It is to be noted that when the methylation frequency (mean value) was 50% or more, it was determined that the concerned region was methylated, and that when the methylation frequency was less than 50%, it was determined that the concerned region was demethylated.

Thereafter, 3 types of malignant melanoma cell lines and 2 types of normal human skin melanocyte cell lines were used, and all of 187 CpG sequences including the binding region of the transcription control factor E2F of the Zar1 gene were examined using MassARRAY. In CpG sequences from the approximately $60^{th}$ CpG and later counted from the 5'-side, in the 187 CpG sequences, a clear difference was found between the methylation of the malignant melanoma cell lines and the methylation of the normal human skin melanocyte cell lines. The results are shown in FIG. 6.

Thereafter, the binding site of the transcription control factor E2F of the Zar1 gene was searched through the UCSC database. As a result, it was found that the binding site is present around a region of CpGs 29-31 in the 187 CpG sequences. Using patient specimens and cell lines, the presence or absence of methylation of this region was examined using MassARRAY. As a result, all the regions were demethylated. The results are shown in FIG. 7. In addition, the same results as described above were obtained also by the Bisulfite Direct Sequence method.

As stated above, a difference in methylation was observed in the CpG sequences from the approximately $60^{th}$ CpG and later, in the 187 CpG sequences existing in the peripheral region of the promoter of the Zar1 gene. In cell lines in which methylation was observed, an increase in the expression of mRNA was observed. Further, demethylation was observed in all of the binding sites of the transcription control factor E2F. From these results, it was assumed that an insulator region acting as an insulator and controlling the functions of an enhancer would be likely to exist in the region from the approximately $60^{th}$ CpG and later, in the peripheral region of the promoter of the Zar1 gene (187 CpG sequences). Several reports have been published so far, concerning expression control by a similar mechanism (Smith J F et al. Epigenetics 2: 161-172, 2007, Daiz-Meyer N et al. J Med Genet 40: 797-801, 2003, Jones P A et al. Trends in Genetics 15: 34-37, 1999).

It has been reported that a CCCTC binding factor (CTCF) binds to all of the insulator regions of vertebrate animals (Bell A C et al. Cell 98: 387-396, 1999). Moreover, a case in which, under the control of DNA methylation, the CTCF controls an enhancer and thereby controls gene expression, has also been reported (Hark A T et al. Nature 405: 486-489, 2000, Bell A C et al. Nature 405: 482-485, 2000).

Hence, the CTCF-binding site (CTCFBS) of the Zar1 gene was searched through CTCF binding site database (http://insulatordb.utmem.edu/search.php). As a result, it was found that there are 5 CTCF-binding sites, and that 2 out of the 5 sites are present in a region in which methylation is observed in malignant tumor cell lines (CTCFBS of FIG. 8).

These putative CTCF-binding sites are methylated at a high frequency in cancer cells. Thus, it is anticipated that the transcription control factor cannot bind to the binding site in cancer cells, and thus that the methylated site does not function as an insulator and an enhancer located downstream or upstream thereof activates the transcription control factor of Zar1, so that the Zar1 is expressed.

As described in the example, cancer-specific methylation is observed at a high frequency in the genomic DNA of the Zar1 gene. Thus, using this methylation as a tumor marker, cancer can be detected at high detection rates and at low false positive rates.

Example 2

Based on the above-described finding that the methylation of the genomic DNA of the Zar1 gene can be used as a cancer marker, it was confirmed in the present example that various types of cancers such as neuroblastoma, pulmonary blastoma and bladder cancer can be detected using the marker.

1. Biological Sample

The following biological samples were used: 22 cases of cryopreserved neuroblastoma patient specimens, which were examined and were subjected to surgery at Pediatric Surgery Section, Itabashi Hospital, Nihon University School of Medicine and which were histopathologically diagnosed as neuroblastoma; 2 cases of cryopreserved patient normal adrenal tissue specimens; 2 cases of cryopreserved patient normal adrenal tissue specimens; 2 neuroblastoma cell lines; 11 cases of cryopreserved patient specimens which were diagnosed as hepatoblastoma; 7 cases of non-tumor portions of hepatoblastoma patient specimens; 2 hepatoblastoma cell lines; the cryopreserved patient specimens of totally surgically removed 7 bladder cancers and partially surgically removed 13 bladder cancers, which were examined and were subjected to surgery at Urological Section, Itabashi Hospital, Nihon University School of Medicine and which were histopathologically diagnosed as bladder cancer; 2 cases of non-tumor bladder portions of bladder cancer patient specimens; and 2 bladder cancer cell lines.

Specimens were collected from patients, after the patients had been explained about specimen collection and written informed consent had been then obtained from all the patients. In addition, the present experiment was approved by the ethics committee of Nihon University School of Medicine and the ethics committee of Itabashi Hospital, Nihon University School of Medicine.

Malignant tumor cell lines TE1, TE2, TE3, TE4, TE5, TE8, TE9, TE11, TE12, TE13, TE15, KE3, KE6 and KE8 (esophageal cancer), SK-N-D2, SK-N-SH, NBLS and KELLY (neuroblastoma), U373 and U118 (glioblastoma), U251 and HS683 (glioma), A431 (cutaneous squamous cell carcinoma), SK-MES-1 (lung squamous cell carcinoma), MCF7 (breast cancer), SAOS and U205 (osteosarcoma), BXPC3 (pancreatic cancer), RKO, LOVO, COLO205, LS180, SW620, HT29 and HCT116 (colon cancer), PC3, 22RV and DU145 (prostatic cancer), J82 (urothelial carcinoma), T24 (bladder cancer), TR126 (squamous cell carcinoma of the tongue), and QMHK11, QMHK10, 4785A, 4785C, 4785D, VIAMM2, 6547A, 3576c1-A and 3576c1-B (unspecified cell lines) were acquired from the Roswell Park Cancer Institute (Buffalo, N.Y., U.S.A.).

A hepatoblastoma cell line HepG2 and a bladder cancer cell line JMSU1 were purchased from RIKEN BioResource Center (Tsukuba-shi, Ibaraki); and a hepatoblastoma cell line HUH6 was purchased from Health Science Research Resources Bank (Sennan-shi, Osaka).

It is to be noted that methods for acquiring A375, COLO829, Hs294T, CRL1579, COLO679, SK-MEL-28, SK-MEL-31, MeWo, Hs695T, Hs839T, NHEM-M, HEMa-LP, NHEM-L and NHEM-D were as described in Example 1.

2. Methods

The same method as that of Example 1 was applied in the present example.

3. Results

The region, in which the DNA methation of ZAR1 was searched in the present example, was the region ranging from CpG118 to CpG166 downstream of a transcription factor-binding site, in a CpG island (the number of CpGs: 187) existing in the promoter region of ZAR1.

Neuroblastoma

Figure 9:
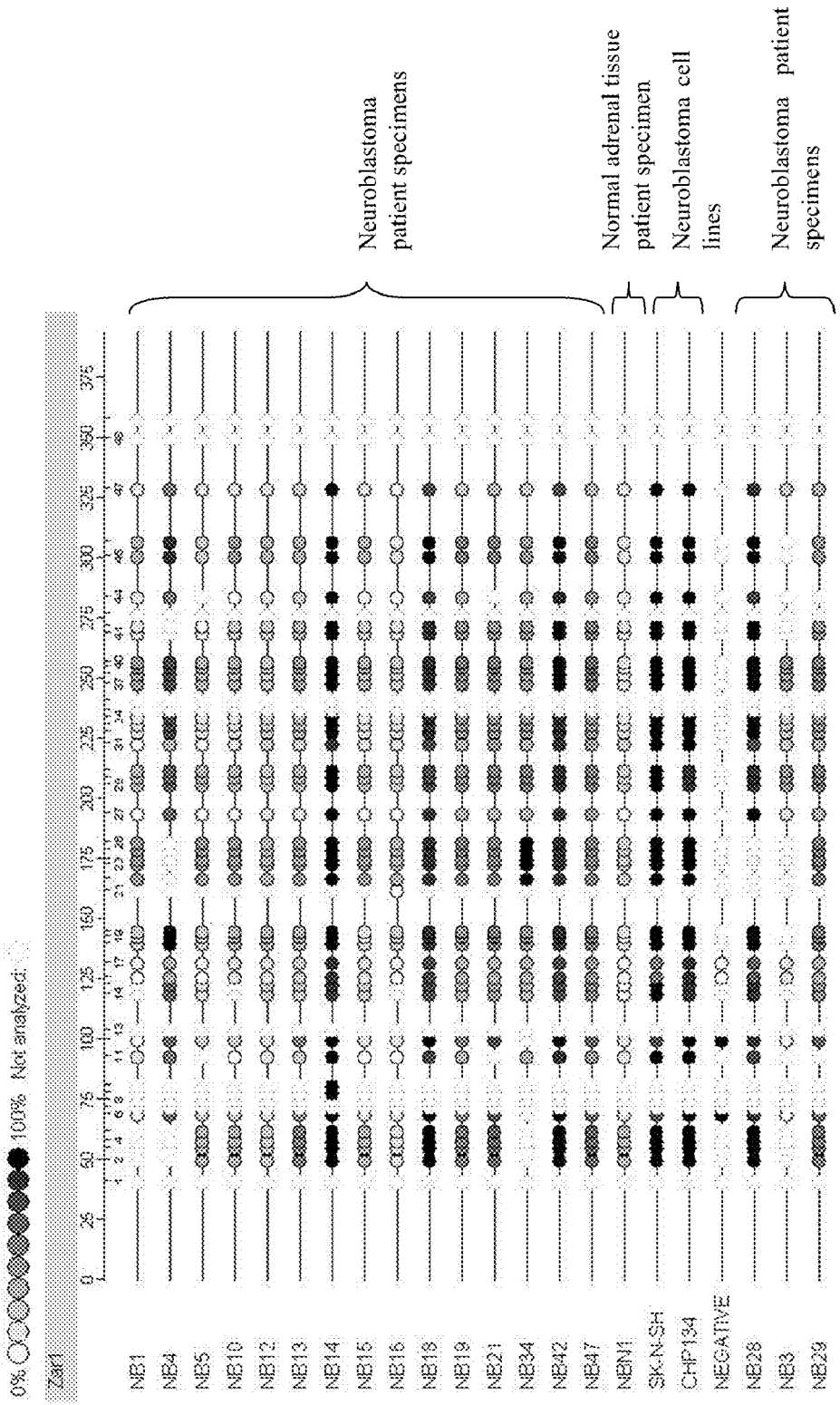
FIG. 9 is a view showing the results obtained by analyzing the genomic DNA of the Zar1 gene, in terms of the presence or absence of methylation.

FIG. 9 is a view showing the details of the results obtained by analyzing the genomic DNA of the Zar1 gene, in terms of the presence or absence of methylation. In 187 CpG sequences existing in the peripheral region of the promoter of the Zar1 gene, the methylation of the $118^{th}$ to $166^{th}$ CpG sequences counted from the 5'-side was analyzed. In addition, FIG. 10 is a graph showing the methylation frequency (mean value) of the $118^{th}$ to $166^{th}$ CpG sequences counted from the 5'-side, in each of neuroblastoma patient specimens (22 cases), neuroblastoma cell lines (2 lines), normal adrenal tissues (2 cases), and normal muscle tissues (2 cases).

Figure 10:
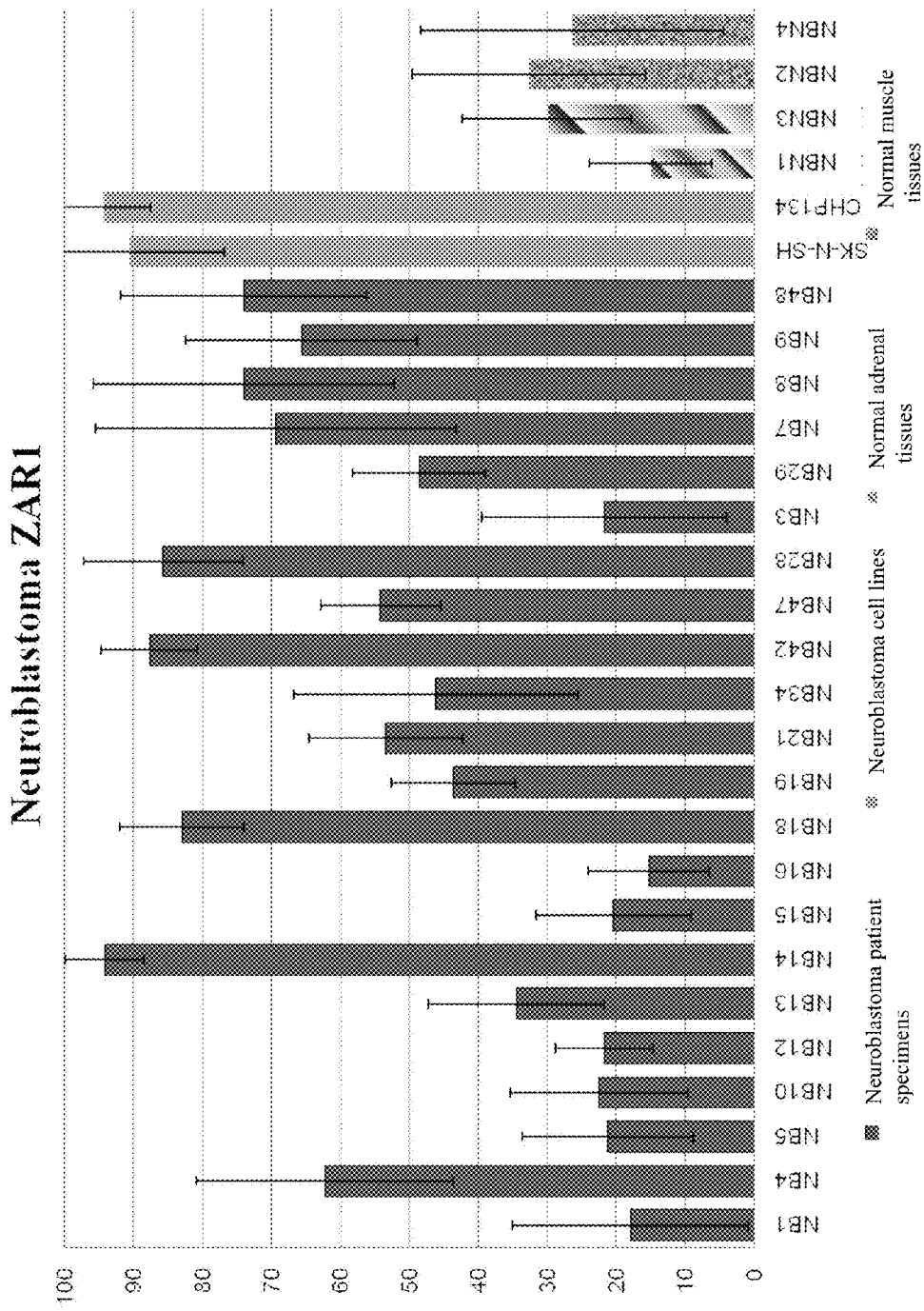
FIG. 10 is a graph showing the methylation frequency (mean value) of the $118^{th}$ to $166^{th}$ CpG sequences counted from the 5'-side in the peripheral region of the promoter of the Zar1 gene in each of 28 types of human-derived samples.

As shown in FIGS. 9 and 10, methylation was observed in 11 out of the 22 neuroblastoma patient specimens and in 2 out of the 2 neuroblastoma cell lines. On the other hand, demethylation was observed in all of the 2 cases of normal adrenal tissues and the 2 cases of normal muscle tissues. It is to be noted that, when the methylation frequency (mean value) was 50% or more, it was determined that the concerned region was methylated. Moreover, when the methylation frequency was less than 50%, it was determined that the concerned region was demethylated.

Hepatoblastoma

Figure 11:
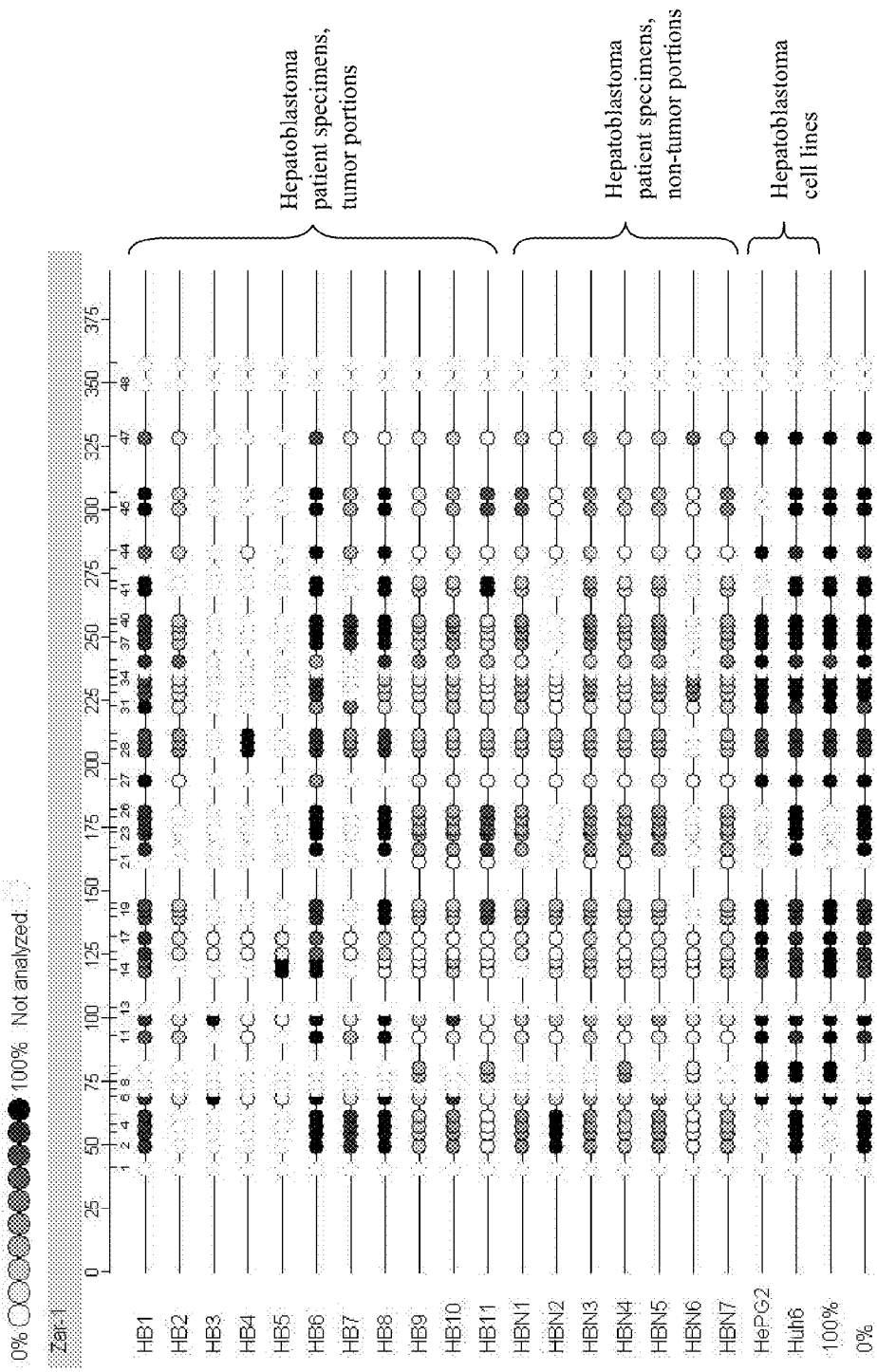
FIG. 11 is a view showing the results obtained by analyzing the genomic DNA of the Zar1 gene, in terms of the presence or absence of methylation.

FIG. 11 is a view showing the details of the results obtained by analyzing the genomic DNA of the Zar1 gene, in terms of the presence or absence of methylation. In 187 CpG sequences existing in the peripheral region of the promoter of the Zar1 gene, the methylation of the $118^{th}$ to $166^{th}$ CpG sequences counted from the 5'-side was analyzed. In addition, FIG. 12 is a graph showing the methylation frequency (mean value) of the $118^{th}$ to $166^{th}$ CpG sequences counted from the 5'-side, in each of the tumor portions of hepatoblastoma patient specimens (11 cases), hepatoblastoma cell lines (2 lines), and the non-tumor portions of hepatoblastoma patient specimens (7 cases).

Figure 12:
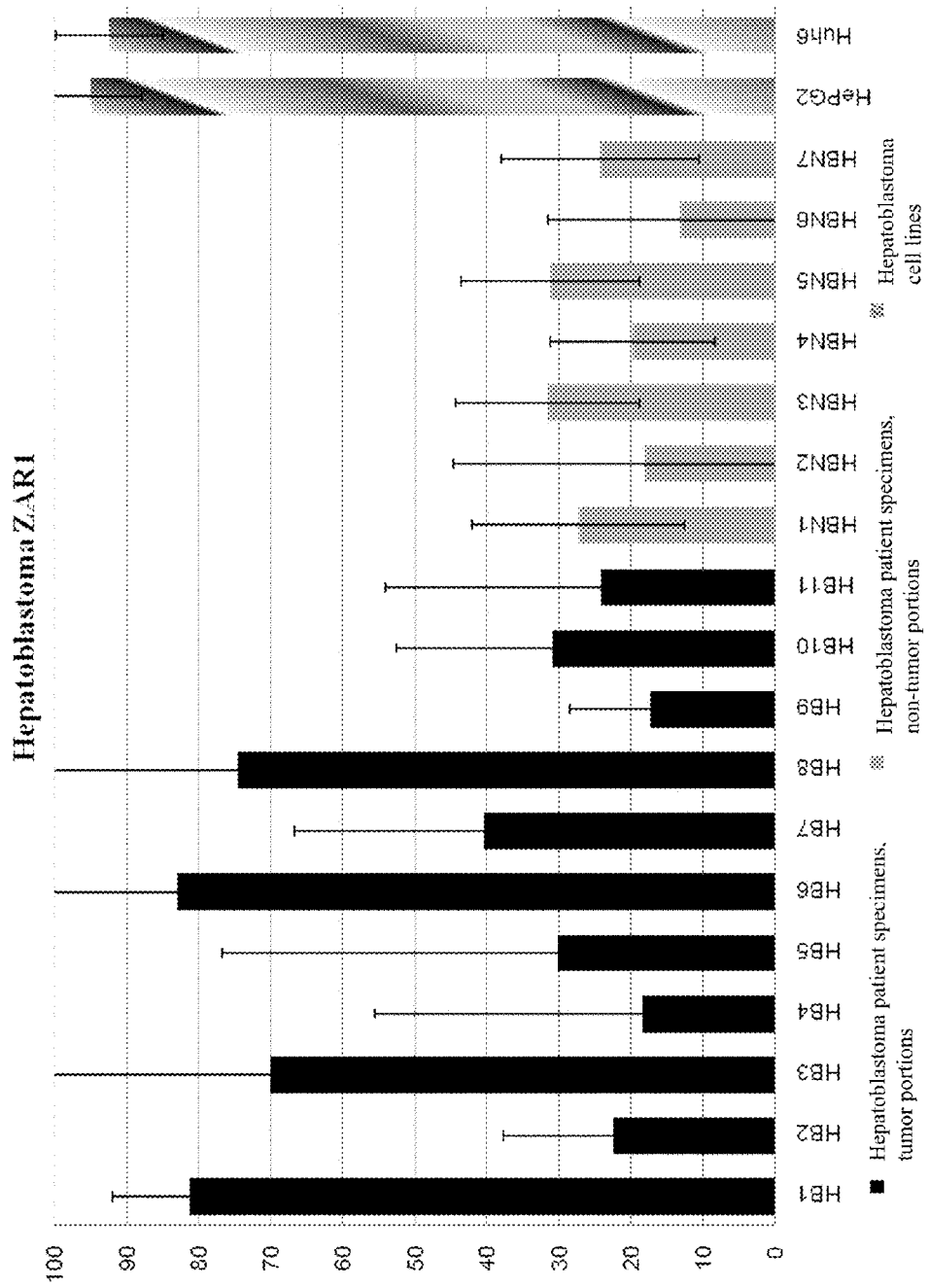
FIG. 12 is a graph showing the methylation frequency (mean value) of the $118^{th}$ to $166^{th}$ CpG sequences counted from the 5'-side in the peripheral region of the promoter of the Zar1 gene in each of 20 types of human-derived samples.

As shown in FIGS. 11 and 12, methylation was observed in 4 out of the 11 cases of tumor portions of hepatoblastoma patient specimens and in 2 out of the 2 hepatoblastoma cell lines. On the other hand, demethylation was observed in all of the 7 cases of non-tumor portions of hepatoblastoma patient specimens. It is to be noted that, when the methylation frequency (mean value) was 50% or more, it was determined that the concerned region was methylated. Moreover, when the methylation frequency was less than 50%, it was determined that the concerned region was demethylated.

Bladder Cancer

Figure 13:
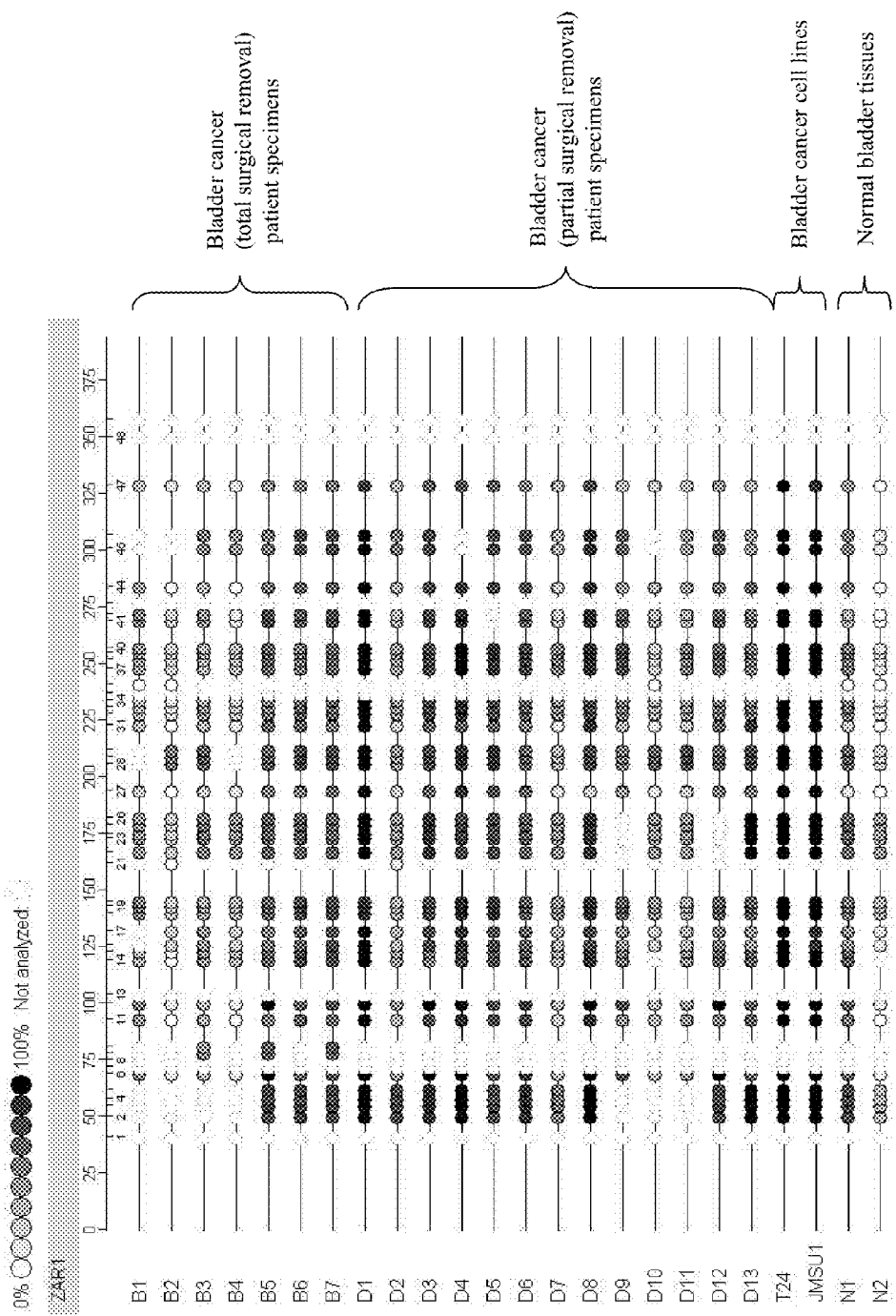
FIG. 13 is a view showing the results obtained by analyzing the genomic DNA of the Zar1 gene, in terms of the presence or absence of methylation.

FIG. 13 is a view showing the details of the results obtained by analyzing the genomic DNA of the Zar1 gene, in terms of the presence or absence of methylation. In 187 CpG sequences existing in the peripheral region of the promoter of the Zar1 gene, the methylation of the $118^{th}$ to $166^{th}$ CpG sequences counted from the 5'-side was analyzed. In addition, FIG. 14 is a graph showing the methylation frequency (mean value) of the $118^{th}$ to $166^{th}$ CpG sequences counted from the 5'-side, in each of totally surgically removed bladder cancer specimens (7 cases), partially surgically removed bladder cancer specimens (13 cases), bladder cancer cell lines (2 lines), and normal bladder tissues (2 cases).

Figure 14:
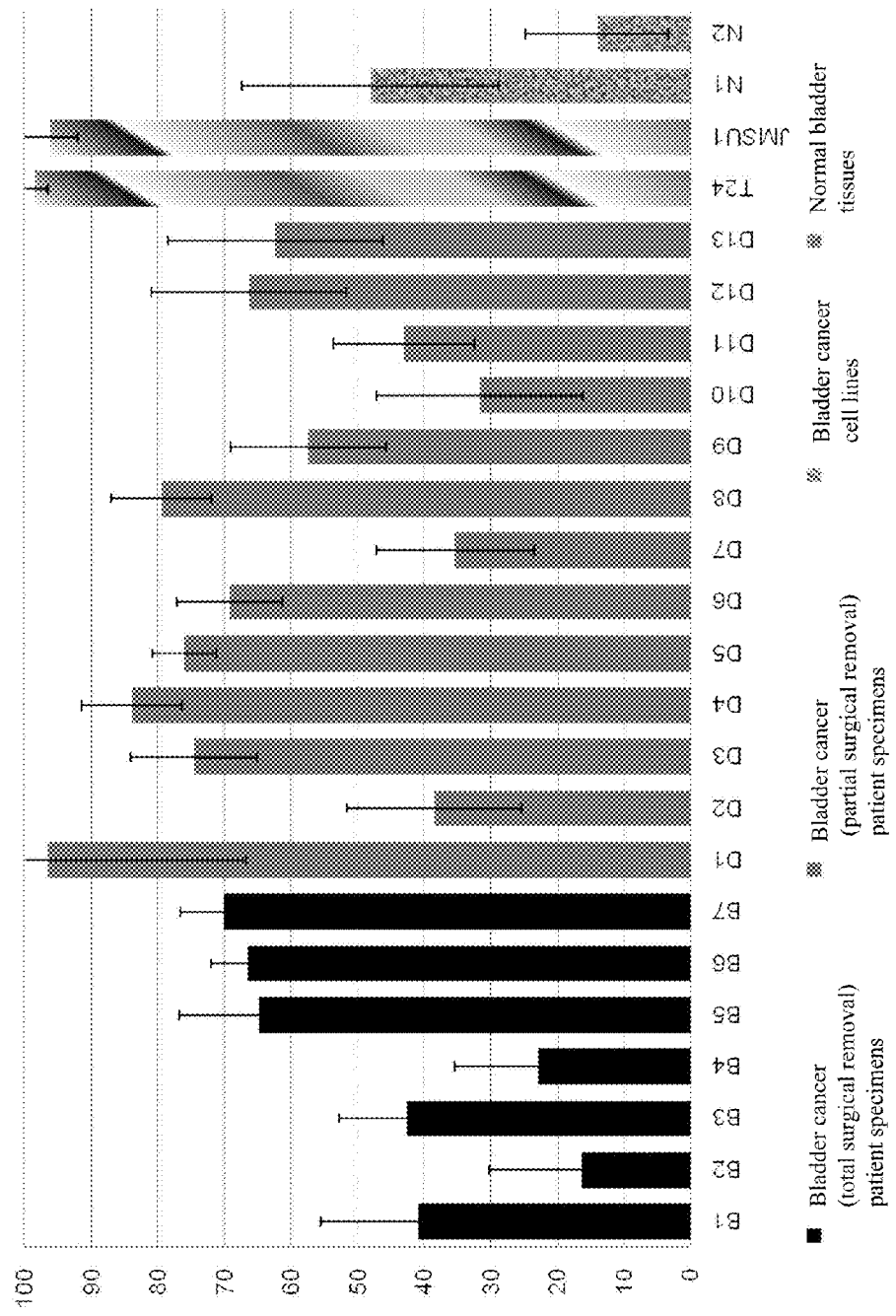
FIG. 14 is a graph showing the methylation frequency (mean value) of the $118^{th}$ to $166^{th}$ CpG sequences counted from the 5'-side in the peripheral region of the promoter of the Zar1 gene in each of 24 types of human-derived samples.

As shown in FIGS. 13 and 14, methylation was observed in 3 out of the 7 cases of totally surgically removed bladder cancer specimens, in 9 out of the 13 cases of partially surgically removed bladder cancer specimens, and in 2 out of the 2 bladder cancer cell lines. On the other hand, demethylation was observed in all of the 2 cases of normal bladder tissues. It is to be noted that, when the methylation frequency (mean value) was 50% or more, it was determined that the concerned region was methylated. Moreover, when the methylation frequency was less than 50%, it was determined that the concerned region was demethylated.

Figure 15:
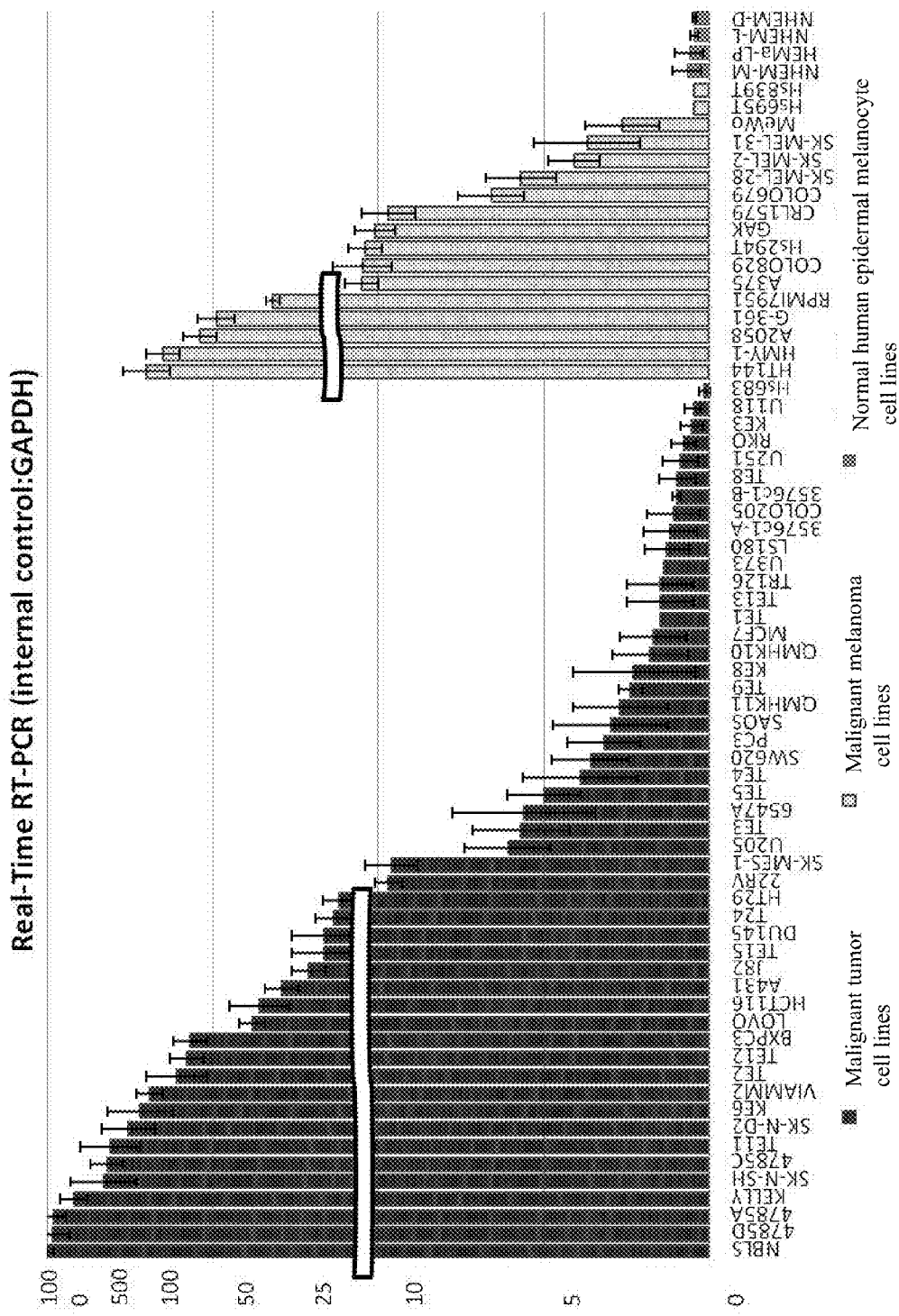
FIG. 15 is a graph showing the results obtained by analyzing 71 types of human-derived samples by real-time RT-PCR, in terms of the expression of the Zar1 gene.

Subsequently, according to real-time RT-PCR, gene expression analyses were performed on 50 types of malignant tumor cell lines, 17 types of malignant melanoma cell lines, and 4 types of normal human skin melanocyte cell lines. A clear increase in the expression of the Zar1 gene was observed in 21 types of malignant tumor cell lines (NBLS, 4785D, 4785A, KELLY, SK-N-SH, 4785C, TE11, SK-N-D2, KE6, VIAMM2, TE2, TE12, BXPC3, LOVO, HCT116, A431, J82, TE15, DU145, T24, and HT29) and in 5 types of malignant melanoma cell lines (G-361, A2058, HMY-1, HT144, and RPMI7951), all of which had been methylated. In contrast, such increase in the expression was not observed in the 4 types of normal human skin melanocyte cell lines, which had been demethylated. The results are shown in FIG. 15.

Sequence Listing Free Text
SEQ ID NO: 4 Synthetic DNA
SEQ ID NO: 5 Synthetic DNA
SEQ ID NO: 6 Synthetic DNA
SEQ ID NO: 7 Synthetic DNA
SEQ ID NO: 8 Synthetic DNA
SEQ ID NO: 9 Synthetic DNA
SEQ ID NO: 10 Synthetic DNA
SEQ ID NO: 11 Synthetic DNA

The invention claimed is:

1. A method for detecting cancer, which comprises:
obtaining a biological sample derived from a human suspected of having cancer, and
detecting the methylation of at least one CpG sequence in a genomic DNA of a Zar1 gene present in the biological sample, the genomic DNA in the region of the $60^{th}$ to $187^{th}$ nucleotides counted from the 5'-side in the peripheral region of the promoter of the Zar1 gene, and
detecting cancer based on the presence of hypermethylation of at least one CpG sequence between the $60^{th}$ to $187^{th}$ nucleotides in said genomic DNA of the Zar1 gene present in the biological sample.

2. The method according to claim 1, which comprises detecting the methylation of at least one CpG sequence selected from among the $118^{th}$ to $166^{th}$ CpG sequences counted from the 5'-side in the peripheral region of the promoter of the Zar1 gene in the human-derived biological sample.

3. The method according to claim 1, wherein the cancer is at least one selected from the group consisting of malignant melanoma, esophageal cancer, neuroblastoma, glioblastoma, glioma, Wilms tumor, cutaneous squamous cell carcinoma, lung adenocarcinoma, lung squamous cell carcinoma, breast cancer, osteosarcoma, rhabdosarcoma, pancreatic cancer, colon cancer, renal cell carcinoma, prostatic cancer, urothelial carcinoma, bladder cancer, cervical cancer, squamous cell carcinoma of the tongue, and hepatoblastoma.

4. The method according to claim 3, wherein the cancer is malignant melanoma, neuroblastoma, hepatoblastoma, or bladder cancer.

5. The method according to claim 1, in which a methylation frequency of the ZAR1 gene in the biological sample is compared with the methylation frequency of the genomic DNA of a ZAR1 gene in a normal cell, and when the methylation frequency of the ZAR1 gene is higher than the methylation frequency of the genomic DNA of the ZAR1 gene in the normal cell, it is determined that the biological sample has become cancerous.

6. The method according to claim 5, in which when the methylation frequency of the ZAR1 gene is 50% or more, it is determined that the biological sample has become cancerous.

* * * * *

SEQUENCE LISTING

```
<160> NUMBER OF SEQ ID NOS: 11

<210> SEQ ID NO 1
<211> LENGTH: 4116
<212> TYPE: DNA
<213> ORGANISM: Homo sapiens
<220> FEATURE:
<221> NAME/KEY: CDS
<222> LOCATION: (1)..(963)
<220> FEATURE:
<221> NAME/KEY: CDS
<222> LOCATION: (2475)..(2567)
<220> FEATURE:
<221> NAME/KEY: CDS
<222> LOCATION: (2647)..(2721)
<220> FEATURE:
<221> NAME/KEY: CDS
<222> LOCATION: (3810)..(3950)

<400> SEQUENCE: 1 atg gcg gcc ctg ggg gac gag gtg ctg gac ggt tac gtg ttc ccg gcg      48
Met Ala Ala Leu Gly Asp Glu Val Leu Asp Gly Tyr Val Phe Pro Ala
1               5                   10                  15 tgc ccc ccc tgc tcg tac cgg tac cca tac ccc gcg gcc acc aag ggc      96
Cys Pro Pro Cys Ser Tyr Arg Tyr Pro Tyr Pro Ala Ala Thr Lys Gly
            20                  25                  30 aag ggc gcg gcg ggc ggc agc tgg cag cag cgc ggc agg ggc tgc ctt     144
Lys Gly Ala Ala Gly Gly Ser Trp Gln Gln Arg Gly Arg Gly Cys Leu
        35                  40                  45 ccc gcc tcc tcc ccc tgc tcg gcg ggc gcg gcc tcg ttg tcc ttc ccg     192
Pro Ala Ser Ser Pro Cys Ser Ala Gly Ala Ala Ser Leu Ser Phe Pro
    50                  55                  60 ggc tgc ggg cgg ctg acg gcc gcc gag tac ttc gac agc tac cag cgg     240
Gly Cys Gly Arg Leu Thr Ala Ala Glu Tyr Phe Asp Ser Tyr Gln Arg
65                  70                  75                  80 gag cgg ctc atg gct ctc ctg gcg cag gtg ggg ccg ggt ctc ggg ccg     288
Glu Arg Leu Met Ala Leu Leu Ala Gln Val Gly Pro Gly Leu Gly Pro
                85                  90                  95 cgc gcc cgc agg gcc ggc agc tgc gac gtg gcg gtg cag gtg agc ccg     336
Arg Ala Arg Arg Ala Gly Ser Cys Asp Val Ala Val Gln Val Ser Pro
            100                 105                 110 cgc atc gac gcc gcg gta cag tgc tcg ctg ggg agg cgc acg ctg cag     384
Arg Ile Asp Ala Ala Val Gln Cys Ser Leu Gly Arg Arg Thr Leu Gln
        115                 120                 125 cgc cgg gcc cgc gac ccc gag tcc ccg gcc ggc ccc ggg gcc gag ggc     432
Arg Arg Ala Arg Asp Pro Glu Ser Pro Ala Gly Pro Gly Ala Glu Gly
    130                 135                 140
```

```
acc acg ggt ggc ggc tct ttc tcc cag cag cca tcc cgt cga ggc ctg    480
Thr Thr Gly Gly Gly Ser Phe Ser Gln Gln Pro Ser Arg Arg Gly Leu
145                 150                 155                 160 gag cag ggc agc ccc cag aac ggc gcc ccg cgg ccc atg cgc ttc ccg    528
Glu Gln Gly Ser Pro Gln Asn Gly Ala Pro Arg Pro Met Arg Phe Pro
                165                 170                 175 cgc acc gtc gcc gtg tac tcg ccc ctg gcc ttg cgc cgt ctc acc gcc    576
Arg Thr Val Ala Val Tyr Ser Pro Leu Ala Leu Arg Arg Leu Thr Ala
            180                 185                 190 ttc ctg gag ggg ccc ggg ccc gcg gcg ggc gag cag agg tcc ggg gcg    624
Phe Leu Glu Gly Pro Gly Pro Ala Ala Gly Glu Gln Arg Ser Gly Ala
        195                 200                 205 tcg gac gga gag agg ggg ccg ccg ccc gcg cgg ctt caa ggc cca gag    672
Ser Asp Gly Glu Arg Gly Pro Pro Pro Ala Arg Leu Gln Gly Pro Glu
    210                 215                 220 gag ggg gag gtg tgg acg aag aag gcg ccc cgg cgg ccg cag tcc gac    720
Glu Gly Glu Val Trp Thr Lys Lys Ala Pro Arg Arg Pro Gln Ser Asp
225                 230                 235                 240 gac gac ggc gag gcc cag gcc gca gtc cga gcg agc tgg gag cag ccg    768
Asp Asp Gly Glu Ala Gln Ala Ala Val Arg Ala Ser Trp Glu Gln Pro
                245                 250                 255 gcc gac ggt ccc gag ctg ccg ccg cga gag gcc cag gag ggc gag gcg    816
Ala Asp Gly Pro Glu Leu Pro Pro Arg Glu Ala Gln Glu Gly Glu Ala
            260                 265                 270 gct ccg cgg tcg gcg cta agg agc ccg ggg caa cct ccg tcg gcg ggg    864
Ala Pro Arg Ser Ala Leu Arg Ser Pro Gly Gln Pro Pro Ser Ala Gly
        275                 280                 285 agg gcc cga gac ggc ggc gac gga cgg gag gcg gcc gtc gcg gga gag    912
Arg Ala Arg Asp Gly Gly Asp Gly Arg Glu Ala Ala Val Ala Gly Glu
    290                 295                 300 ggg ccg tcg cca cgg agc ccg gag ctg ggc aag gag cgg ctg cgc ttc    960
Gly Pro Ser Pro Arg Ser Pro Glu Leu Gly Lys Glu Arg Leu Arg Phe
305                 310                 315                 320 cag gtaaagccta gggcggtcag ggcacagggg agcccggggg tgcgggtgtc         1013
Gln ttccttgggc ctggccctgt gactgcttcg ggcactcgga ggtgcggcgc ttccctaagc  1073
gtgggctact tccgtatttc cgagacagcc aatgaccgcg ataggtgtct ccttgacag   1133 cacagtctca tgtccccgac atccagactt actcgtggcg gctgctccac gggctggcca  1193
gggcgacgcc cttgggacgt tcttataacc cacatatttg cactgtaaac ctcgcgcagt  1253
gggcgcatag gccagccctg accgcacggt tggattacct atcagtaggc acaactgaac  1313
ttcggagcac ttgccggctg gagagtcgat tcccaaggat ccctctctcc catttccgca  1373
ctggatgtgg caaaaccct tcaactgctg ggattctggt cagcaattct gatttctcct   1433
ttacgagctt ccaggctatt ggaaagctgg agctcctaaa atgccccttc ctaggaattt  1493
gctttgcttt taagaagcac ccccaactca gaaatccaat actgcgaaag catttggact  1553
gctcagtgtt gctgcccgag ggcagcaggc tgaaacttta aagggctggg gcacgcagag  1613
ggcagttgtg acctagcaga agtggaaagg cacaagaggt ggtaagaagc ccgagggagt  1673
ccctcgcggt ctcttccacg gccaccacag gctggtattc cttttgaggg gcggggttgg  1733
tggcggtagg ctgattgtgc gaggagtgaa tcgagaggcc agggcttccc agcgtggctg  1793
tgcaggagct gtgtgtgatc ttaggccagt cataaccttc ctggacttag cgcagtctca  1853
caggtgagca gactgaatta agtgctcccc agagttcctt ccaattctga aaggctaact  1913
ctaaaaacgt gtgcataact gcttgcttac tgggagggaa gaagggaagt ttaagtaaca  1973
```

```
ctactttgt tcatattgaa tatgaattat ggcttacgta cgatttaggt tcctggcacc      2033
actgtttggg agttaactag cagcatgaag aatgtgatct tgggtgaacc tttaaagttc      2093
cttagatgtg gagtcttatt tttcttcagc ttaatacatg tgtgcatagt ctaagatcag      2153
gctttatctt aaaaggcctt cctacagaat cccaaacttt agagaactgt ttattatgtc      2213
cctacttatt cgtttattag ccagccttat gaactgagtt aatctggtat atgaactcta      2273
aggcccatgc ttgcttaatt gtttgactag gctattaagc tcacttaatt actgtattga      2333
agaggcgtac ccaaacctga cctgctttct ttcatgatct gaagttgcca atttcaaata      2393
tcaagtagat ccttcccaac gtctgaaatg aaggataatt caggtgtttt gttggttaaa      2453
ttgacatatc ctgttgttca g ttc tta gag cag aaa tat ggc tat tac cac       2504
                       Phe Leu Glu Gln Lys Tyr Gly Tyr Tyr His
                                    325                 330 tgc aag gac tgc aac atc cgc tgg gag agt gct tat gtg tgg tgt gta       2552
Cys Lys Asp Cys Asn Ile Arg Trp Glu Ser Ala Tyr Val Trp Cys Val
            335                 340                 345 cag gga act aac aag gtaagaaata ccaggtaact ggcatcttct tgctgaaagt       2607
Gln Gly Thr Asn Lys
350 gtcaaggcga ttttaagttt atcctctttg tcatcacag gtt tac ttc aaa cag         2661
                                           Val Tyr Phe Lys Gln
                                                    355 ttt tgc aga act tgt cag aag tct tat aac cct tac cga gtg gag gat       2709
Phe Cys Arg Thr Cys Gln Lys Ser Tyr Asn Pro Tyr Arg Val Glu Asp
            360                 365                 370 atc acc tgt caa gtaaatcaga tgttttgcat tttgtctgac ctgggcagtc           2761
Ile Thr Cys Gln
        375 gtcgagggtt tttagtatag tttgagtata cttccaaaaa gaggccaggc ccccagacct      2821 taggtttcaa ctggcttttg ttaggagtgg tagaaacaat actcagctgg gaaacggggc      2881 cttggtgtta gcttctttct ggccttgcaa atcttgctgt tgttaacctc ttctaaaact      2941 gttaacctca cttgcaatat ggaagaatac ttgtcttact tgctacttag tctaatgtat      3001 aagaaaatca acaaaaacat gcttgtcagc taacatgagg tagtcaaggt tgactgtttt      3061 accgaaacgc ttcttatgaa gcacaacctt aaagtactta agcacagggg gttagtttgt      3121 cttgcctgaa agctcacaaa gggacagttt aagataaatc taagttgtct agctttatgg      3181 ggagttgact ataatggtaa gcaagcaata tgttaactaa gcattgctta agcgcttgct      3241 tgctattaac tgtgctaagg ggcttagcta atctttaaga ggaaagaagt gactacattc      3301 gcctcttgtc acacagctaa tggagtctga attgccagtt gagacagcct aatcaataca      3361 cttgacccac gttggatatt taaaagcatt aacaccctgg ggtggtggag agaaactaag      3421 tatggaaagc cacttagaat cacttagatc agagctgggc atgtttctaa aagaggatgc      3481 cttaaccact ctgctcttgg tgttcattgt caaattcatc cctgacttgt tctctacccct     3541 ttctcttaaa cagttgttgt aaaagaaatt tcacaattca taattggatc tgatgcaata      3601 tagcagcagt acagcatggt taaacaccca ctattcctag ccctgtcatt gctacgtagg      3661 tagggatgta gagggaaaac aagattacta tgggaccttg cttagagcac attcattaag      3721 tacttgaatg gactagaaaa atgttgaagt cctaggaaat cactaagggt ttatcttctg      3781 catgcccttc tgtatttttt tcccccag agt tgt aaa caa acg aga tgt tcc        3833
                                Ser Cys Lys Gln Thr Arg Cys Ser
                                        380                 385 tgc cca gta aaa ctt cgc cac gtg gac cct aaa cgg ccc cac cgt caa       3881
Cys Pro Val Lys Leu Arg His Val Asp Pro Lys Arg Pro His Arg Gln
```

```
                       390                 395                 400
gat ttg tgc ggt aga tgc aaa ggc aaa cgc ctg tcc tgt gac agc act        3929
Asp Leu Cys Gly Arg Cys Lys Gly Lys Arg Leu Ser Cys Asp Ser Thr
        405                 410                 415 ttc agc ttc aaa tac atc att taggtgaaag tcagtgttgc tgtgcatgcg           3980
Phe Ser Phe Lys Tyr Ile Ile
        420 ctgatggagt agacgagtga gcttttccgt gcctctcctc cacctctccc ttctcaaaat      4040 acttcatgaa aggcagtgta ttctgaaaaa gccttcaaat aaaggtattg caacacgatt      4100 tatacattgc ataaaa                                                     4116

<210> SEQ ID NO 2
<211> LENGTH: 424
<212> TYPE: PRT
<213> ORGANISM: Homo sapiens

<400> SEQUENCE: 2

Met Ala Ala Leu Gly Asp Glu Val Leu Asp Gly Tyr Val Phe Pro Ala
1               5                   10                  15

Cys Pro Pro Cys Ser Tyr Arg Tyr Pro Tyr Pro Ala Ala Thr Lys Gly
            20                  25                  30

Lys Gly Ala Ala Gly Ser Trp Gln Gln Arg Gly Arg Gly Cys Leu
        35                  40                  45

Pro Ala Ser Ser Pro Cys Ser Ala Gly Ala Ala Ser Leu Ser Phe Pro
    50                  55                  60

Gly Cys Gly Arg Leu Thr Ala Ala Glu Tyr Phe Asp Ser Tyr Gln Arg
65                  70                  75                  80

Glu Arg Leu Met Ala Leu Leu Ala Gln Val Gly Pro Gly Leu Gly Pro
                85                  90                  95

Arg Ala Arg Arg Ala Gly Ser Cys Asp Val Ala Val Gln Val Ser Pro
            100                 105                 110

Arg Ile Asp Ala Ala Val Gln Cys Ser Leu Gly Arg Arg Thr Leu Gln
        115                 120                 125

Arg Arg Ala Arg Asp Pro Glu Ser Pro Ala Gly Pro Gly Ala Glu Gly
    130                 135                 140

Thr Thr Gly Gly Gly Ser Phe Ser Gln Gln Pro Ser Arg Arg Gly Leu
145                 150                 155                 160

Glu Gln Gly Ser Pro Gln Asn Gly Ala Pro Arg Pro Met Arg Phe Pro
                165                 170                 175

Arg Thr Val Ala Val Tyr Ser Pro Leu Ala Leu Arg Arg Leu Thr Ala
            180                 185                 190

Phe Leu Glu Gly Pro Gly Pro Ala Ala Gly Glu Gln Arg Ser Gly Ala
        195                 200                 205

Ser Asp Gly Glu Arg Gly Pro Pro Ala Arg Leu Gln Gly Pro Glu
    210                 215                 220

Glu Gly Glu Val Trp Thr Lys Lys Ala Pro Arg Arg Pro Gln Ser Asp
225                 230                 235                 240

Asp Asp Gly Glu Ala Gln Ala Val Arg Ala Ser Trp Glu Gln Pro
                245                 250                 255

Ala Asp Gly Pro Glu Leu Pro Pro Arg Glu Ala Glu Gly Glu Ala
            260                 265                 270

Ala Pro Arg Ser Ala Leu Arg Ser Pro Gly Gln Pro Pro Ser Ala Gly
        275                 280                 285

Arg Ala Arg Asp Gly Gly Asp Gly Arg Glu Ala Ala Val Ala Gly Glu
    290                 295                 300
```

```
Gly Pro Ser Pro Arg Ser Pro Glu Leu Gly Lys Glu Arg Leu Arg Phe
305                 310                 315                 320

Gln Phe Leu Glu Gln Lys Tyr Gly Tyr Tyr His Cys Lys Asp Cys Asn
            325                 330                 335

Ile Arg Trp Glu Ser Ala Tyr Val Trp Cys Val Gln Gly Thr Asn Lys
        340                 345                 350

Val Tyr Phe Lys Gln Phe Cys Arg Thr Cys Gln Lys Ser Tyr Asn Pro
    355                 360                 365

Tyr Arg Val Glu Asp Ile Thr Cys Gln Ser Cys Lys Gln Thr Arg Cys
370                 375                 380

Ser Cys Pro Val Lys Leu Arg His Val Asp Pro Lys Arg Pro His Arg
385                 390                 395                 400

Gln Asp Leu Cys Gly Arg Cys Lys Gly Lys Arg Leu Ser Cys Asp Ser
                405                 410                 415

Thr Phe Ser Phe Lys Tyr Ile Ile
                420

<210> SEQ ID NO 3
<211> LENGTH: 1800
<212> TYPE: DNA
<213> ORGANISM: Homo sapiens

<400> SEQUENCE: 3
tcatctgagt taacgggtaa tagacccaga acagttccca aaccttggca ctttcgctca      60
cttagccaga ggcacccggc ctggcctcgg cttcccggtg agggagcggg ggtgggggg     120 atgcgcaggc acctggaaca atcagggcac cgggagaagc cggctcagct gatgccggtg    180
atgagtttct ctcattgaaa tcctcctcac ctcgggcgcc ttggttccct tacgdatcag    240 cccttcatc acaaagaaag ccctcttcc agatcatcta agggtcattg tgccaacatc      300
cgggcgtgga gagtttctgt agggagaagg acgaagaggg gcccctcgg cggggacgcg     360 ggccggtggc aggaagggcg tggagggcgg tgcagcgtgc gagcccccgc cgagggccat    420
ccccgcctcc gctcggccgc ccgggcaagt cgcctattta gggtgcggcg gcgggcggga    480
gcagtgcgcc catggcggcc ctgggggacg aggtgctgga cggttacgtg ttcccggcgt    540 gcccccctg ctcgtaccgg tacccatacc ccgcggccac caagggcaag ggcgcggcgg     600
gcggcagctg gcagcagcgc ggcaggggct gccttcccgc ctcctccccc tgctcggcgg    660
gcgcggcctc gttgtccttc ccgggctgcg ggcggctgac ggccgccgag tacttcgaca    720
gctaccagcg ggagcggctc atggctctcc tggcgcaggt ggggccgggt ctcgggccgc    780
gcgcccgcag ggccggcagc tgcgacgtgg ccgtgcaggt gagcccgcgc atcgacgccg    840
cggtacagtg ctcgctgggg aggcgcacgc tgcagcgccg ggcccgcgac cccgagtccc    900
cggccggccc cggggccgag ggcaccacgg gtggcggctc tttctcccag cagccatccc    960
gtcgaggcct ggagcagggc agcccccaga acggcgcccc gcggcccatg cgcttcccgc   1020
gcaccgtcgc cgtgtactcg cccctggcct tgcgccgtct caccgccttc ctggagggc    1080 ccgggccgc ggcgggcgag cagaggtccg gggcgtcgga cggagagagg gggccgccgc   1140
ccgcgcggct tcaaggccca gaggaggggg aggtgtggac gaagaaggcg cccggcggc    1200 cgcagtccga cgacggc gaggcccagg ccgcagtccg agcgagctgg agcagccgc       1260 ccgacggtcc cgagctgccg ccgcgagagg cccaggaggg cgaggcggct ccgcggtcgg   1320
cgctaaggag cccggggcaa cctccgtcgg cggggagggc ccgagacggc ggcgacggac   1380
gggaggcggc cgtcgcggga gagggccgt cgccacggag cccggagctg gcaaggagc    1440
```

```
ggctgcgctt ccaggtaaag cctagggcgg tcagggcaca ggggagcccg ggggtgcggg    1500
tgtcttcctt gggcctggcc ctgtgactgc ttcgggcact cggaggtgcg gcgcttccct    1560
aagcgtgggc tacttccgta tttccgagac agccaatgac cgcgataggt gtcttccttg    1620
acagcacagt ctcatgtccc cgacatccag acttactcgt ggcggctgct ccacgggctg    1680
gccagggcga cgcccttggg acgttcttat aacccacata tttgcactgt aaacctcgcg    1740
cagtgggcgc ataggccagc cctgaccgca cggttggatt acctatcagt aggcacaact    1800
```

<210> SEQ ID NO 4
<211> LENGTH: 10
<212> TYPE: DNA
<213> ORGANISM: Artificial sequence
<220> FEATURE:
<223> OTHER INFORMATION: synthetic DNA

<400> SEQUENCE: 4
aggaagagag                                                            10

<210> SEQ ID NO 5
<211> LENGTH: 31
<212> TYPE: DNA
<213> ORGANISM: Artificial sequence
<220> FEATURE:
<223> OTHER INFORMATION: synthetic DNA

<400> SEQUENCE: 5
cagtaatacg actcactata gggagaaggc t                                    31

<210> SEQ ID NO 6
<211> LENGTH: 25
<212> TYPE: DNA
<213> ORGANISM: Artificial sequence
<220> FEATURE:
<223> OTHER INFORMATION: synthetic DNA

<400> SEQUENCE: 6
aatatggcta ttaccactgc aagga                                           25

<210> SEQ ID NO 7
<211> LENGTH: 23
<212> TYPE: DNA
<213> ORGANISM: Artificial sequence
<220> FEATURE:
<223> OTHER INFORMATION: synthetic DNA

<400> SEQUENCE: 7
ggcaggaaca tctcgtttgt tta                                             23

<210> SEQ ID NO 8
<211> LENGTH: 20
<212> TYPE: DNA
<213> ORGANISM: Artificial sequence
<220> FEATURE:
<223> OTHER INFORMATION: synthetic DNA

<400> SEQUENCE: 8
gcaccgtcaa ggctgagaac                                                 20

<210> SEQ ID NO 9
<211> LENGTH: 19
<212> TYPE: DNA
<213> ORGANISM: Artificial sequence
<220> FEATURE:
<223> OTHER INFORMATION: synthetic DNA

```
<400> SEQUENCE: 9
tggtgaagac gccagtgga                                            19

<210> SEQ ID NO 10
<211> LENGTH: 24
<212> TYPE: DNA
<213> ORGANISM: Artificial sequence
<220> FEATURE:
<223> OTHER INFORMATION: synthetic DNA

<400> SEQUENCE: 10
tttggagtag ggtagttttt agaa                                      24

<210> SEQ ID NO 11
<211> LENGTH: 22
<212> TYPE: DNA
<213> ORGANISM: Artificial sequence
<220> FEATURE:
<223> OTHER INFORMATION: synthetic DNA

<400> SEQUENCE: 11 cccctcctc taaaccttaa aa                                         22
```